US007309578B2

(12) United States Patent
D'Armiento et al.

(10) Patent No.: US 7,309,578 B2
(45) Date of Patent: Dec. 18, 2007

(54) THERAPEUTIC TREATMENT OF CHRONIC OBSTRUCTIVE PULMONARY DISEASE

(75) Inventors: Jeanine D'Armiento, New York, NY (US); Kazushi Imai, Tokyo (JP)

(73) Assignee: The Trustees of Columbia University in the City of New York, New York, NY (US)

( * ) Notice: Subject to any disclaimer, the term of this patent is extended or adjusted under 35 U.S.C. 154(b) by 546 days.

(21) Appl. No.: 10/204,496

(22) PCT Filed: Feb. 28, 2001

(86) PCT No.: PCT/US01/06579

§ 371 (c)(1),
(2), (4) Date: May 19, 2003

(87) PCT Pub. No.: WO01/64717

PCT Pub. Date: Sep. 7, 2001

(65) Prior Publication Data

US 2003/0215420 A1 Nov. 20, 2003

Related U.S. Application Data

(63) Continuation-in-part of application No. 09/514,885, filed on Feb. 29, 2000, now Pat. No. 6,656,461.

(51) Int. Cl.
*G01N 33/50* (2006.01)
*C12Q 1/68* (2006.01)
*C12Q 1/37* (2006.01)
*C12Q 1/48* (2006.01)

(52) U.S. Cl. .......................... 435/7.21; 435/6; 435/7.4; 435/15; 435/24

(58) Field of Classification Search ..................... None
See application file for complete search history.

(56) References Cited

U.S. PATENT DOCUMENTS 5,824,551 A 10/1998 Damme et al.

OTHER PUBLICATIONS

Zhang et al. Cell cultures from bronchial subepithelial myofibroblasts enhance eosinophil survival in vitro. Eur Respir J. Sep. 1996;9(9):1839-46.*

Woolley et al. Eosinophil apoptosis and the resolution of airway inflammation in asthma. Am J Respir Crit Care Med. Jul. 1996;154(1):237-43.*

Spinozzi et al. Defective expression of Fas messenger RNA and Fas receptor on pulmonary T cells from patients with asthma. Ann Intern Med. Mar. 1, 1998;128(5):363-9.*

Vignola et al. Evaluation of apoptosis of eosinophils, macrophages, and T lymphocytes in mucosal biopsy specimens of patients with asthma and chronic bronchitis. J Allergy Clin Immunol. Apr. 1999;103(4):563-73.*

Niewoehner DE. What lies ahead? Future research and treatment for chronic obstructive pulmonary disease. Am J Med. Oct. 21, 1991;91(4A):41S-46S.*

Cardone MH, et al.: Regulation of Cell Death Protease Caspase-9 by Phosphorylation. *Science*. vol. 282, No. 5392, Nov. 13, 1998, pp. 1318-1321 (Exhibit 2).

D'Armeinto J, et al.: Collagenase Expression in the Lungs of Transgenic Mice Causes Pulmonary Emphysema. *Cell*. vol. 71, No. 6, Dec. 11, 1992, pp. 955-961 (Exhibit 3).

Dale TC: Signal transduction by the Wnt family of ligands. *Biochem. J.* (1998) , vol. 329, pp. 209-223 (Exhibit 4).

Dunnill MS, et al.: Quantitative Methods In The Study Of Pulmonary Pathology. *Thorax*. vol. 17, 1962, pp. 320-328 (Exhibit 5).

Feinleib M, et al.: Trends in COPD Morbidity and Mortality in the United States. *Am. Rev. Respir. Dis*. vol. 140, No. 3, Pt. 2, Sep. 1989, pp. S9-S18 (Exhibit 6).

Finch PW, et al.: Purification and molecular cloning of a secreted, Frizzled-related antagonist of Wnt action. *Proc. Natl. Acad. Sci. USA*. vol. 94, Jun. 24, 1997, pp. 6770-6775 (Exhibit 7).

Frisch SM and Ruoslahti E: Integrins and Anoikis. *Curr. Opin. in Cell Biol*. vol. 9, No. 5, Oct. 1997, pp. 701-706 (Exhibit 8).

From the centers for disease control and prevention: Mortality Patterns-United States, 1991. *JAMA*. vol. 270, No. 24, Dec. 22, 1993, pp. 2916-2917 (Exhibit 9).

Granville DJ, et al.: Apoptosis: Molecular Aspects of Cell Death and Disease. *Lab. Invest*. vol. 78, No. 8, Aug. 1998, pp. 893-913 (Exhibit 10).

Hautamaki RD, et al.: Requirement of macrophage elastase for cigarette smoke-induced emphysema in mice. *Science*. vol. 277, Sep. 26, 1997, pp. 2002-2004 (Exhibit 11).

(Continued)

*Primary Examiner*—David Romeo
(74) *Attorney, Agent, or Firm*—John P. White; Cooper & Dunham LLP

(57) ABSTRACT

The present invention provides a method of treating or preventing a chronic obstructive pulmonary disease in a subject, comprising administering to said subject an amount of an agent affective to inhibit apoptosis of the subject's lung cells and thus treat or prevent chronic obstructive pulmonary disease in the subject. The present invention provides for a method of diagnosing the disease. Also, the invention provides a method for identifying a compound effective to treat or prevent a chronic obstructive pulmonary disease, comprising (a) contacting lung cells from a subject having a chronic obstructive pulmonary disease with the compound and measuring the level of apoptosis of the lung cells in the presence of said compound, (b) measuring the level of apoptosis of the lung cells from the same subject in the absence of said compound, (c) comparing the level of apoptosis in step (a) with the level of apoptosis in step (b), wherein a higher level of apoptosis in step (b) indicate that the compound is effective to treat or prevent chronic obstructive pulmonary disease.

6 Claims, 23 Drawing Sheets

OTHER PUBLICATIONS

Hoang B, et al.: Primary structure and tissue distribution of FRZB, a novel protein related to Drosophilia frizzled, suggest a role in skeletal morphogenesis. *J Biol Chem*. vol. 271, No. 42, Oct. 18, 1996, pp. 26131-26137 (Exhibit 12).
Hoidal JR and Niewoehner DE: Pathogenesis of Emphysema. *Chest*. vol. 83, No. 4, Apr. 1983, pp. 679-685 (Exhibit 13).
Imai K: and D'Armiento J: Activation of an Embryonic Gene Product in Pulmonary Emphysema. *Am. Rev. Resp. Crit. Care Med*. vol. 159, 1983.
Imai K, et al.: Expression of Membrane-Type 1 Matrix Metalloproteinase and Activation of Progelatinase A in Human Osteoarthritic Cartilage. *Am J. Pathol*. vol. 151, No. 1, Jul. 1997, pp. 245-256 (Exhibit 15).
Leyns L, et al.: Frzb-1 is a secreted antagonist of Wnt signaling expressed in the Spemann organizer. *Cell* vol. 88, No. 6, Mar. 21, 1997, pp. 747-756 (Exhibit 16).
Luisetti M, et al.: MR889, a neutrophil elastase inhibitor, in patients with chronic obstructive pulmonary disease: a double-blind, randomized, placebo-controlled clinical trial. *Eur. Resp. J*. vol. 9, No. 7, Jul. 1996, pp. 1482-1486 (Exhibit 17).
Melkonyan HS, et al.: SARPs: A family of secreted apoptosis-related proteins. *Proc. Natl. Acad. Sci. USA*. vol. 94, No. 25, Dec. 9, 1997, pp. 13636-13641: (Exhibit 18).
Petitclerc E, et al.: Integrin $AB_3$ Promotes M21 Melanoma Growth in Human Skin by Regulating Tumor Cell Survival. *Cancer Research*. vol. 59, No. 11, Jun. 1, 1999, pp. 2724-2730. (Exhibit 19).
Putt F: *Manual of Histopathological Staining Methods*, Wiley and Sons (New York), (1972), pp. 111-126 (Exhibit 20).
Rattner A, et al.: A family of secreted proteins contains homology to the cysteine-rich ligand-binding domain of frizzled receptors. *Proc Natl Acad Sci USA*. vol. 94, No. 7, Apr. 1, 1997, pp. 2859-2863 (Exhibit 21).
Rudin CM and Thompson CB: Apoptosis and Disease: Regulation and Clinical Relevance of Programmed Cell Death. *Annu. Rev. Med*. vol. 48, 1997, pp. 267-281 (Exhibit 22).
Sharpiro SD: The Pathogenesis of Emphysema: the Elastase: Antielastase Hypothesis 30 years later. *Proc. Ass. Amer. Phys*. vol. 107, No. 3, Oct. 1995, pp. 346-352 (Exhibit 23).
Snider GL: Chronic Obstructive Pulmonary Disease: Risk Factors, Pathophysiology and Pathogenesis. *Annu. Rev. Med*. vol. 40, 1989, pp. 411-429 (Exhibit 24).
Snider GL, et al.: Pitfalls in Antiprotease Therapy of Emphysema *Am. J. Respir. Crit. Care Med*. vol. 150, No. 6, Pt. 2, Dec. 1994, pp. S131-S137 (Exhibit 25).
Tetley TD: Proteinase imbalance: its role in the lung disease. *Thorax*. vol. 48, No. 5, May 1993, pp. 560-565 (Exhibit 26).
Tetsu O and McCormick F: b-catenin regulates expression of cyclin D1 in colon carcinoma cells. *Nature*. vol. 398, No. 6726, Apr. 1, 1999, pp. 422-426 (Exhibit 27).
Thurlbeck WM: Internal surface area and other measurements in emphysema. *Thorax*. vol. 22, No. 6, Nov. 1967, pp. 483-496 (Exhibit 28).
Tomkeieff SE: Linear Intercepts, Areas and Volumes. *Nature*. vol. 155, Jan. 6, 1945, pp. 105-111 (Exhibit 29).
Wolf BB and Green DR: Suicidal Tendencies: Apoptotic Cell Death by Caspase Family Proteinases *J. Biol. Chem*. vol. 274, No. 29, Jul. 16, 1999, pp. 20049-20052 (Exhibit 30).
Wyllie AH: Cell Death: The Significance of Apoptosis. *Int. Rev. Cytol*. vol 68, 1980, pp. 251-306 (Exhibit 31).
Zhou Z, et al.: Up-Regulation of Human Secreted Frizzled Homolog in Apoptosis and its Down-Regulation in Breast Tumors. *Int. J. Cancer*. vol. 78, No. 1, Sep. 25, 1998, pp. 95-99 (Exhibit 32).
Vignola, AM et al., Evaluation of apoptosis of eosinophils, macrophages, and T lymphocytes in mucosal biopsy specimens of patients with asthma and chronic bronchitis, *J Allergy Clin. Immunol*, Apr. 1999, pp. 563-573 (Exhibit 33).
Yasuda, N. An increase of soluble Fas, an inhibitor of apoptosis, associated with progression of COPD, *Respiratory Medicine* (1998), vol. 92, pp. 993-999 (Exhibit 34).
Goya et al. Identification of CCR8 an the specific receptor for the human beta-chemokine T-309: cloning and molecular characterization of murine CCR8 as the receptor for TCA J. J. Immunol. Feb. 15, 1998; 160(4):1975-81 (Exhibit 35).
Haslett C. Granulocyte apoptosis and its role in the resolution and control of lung inflammation. Am. J. Respir Crit Care Med. Nov. 1999; 160 (5 Pt 2) : S5-11 (Exhibit 36).
Murdoch et al., Chemokine receptors and their role in inflammation and infectious diseases. Blood May 15, 2000; 95 (10) : 3032-43 (Exhibit 37).
Proost et al. Human monocyte chemotatic proteins-2 and -3: structural and functional comparison with MCP-1. J. Leukoc Biol. Jan. 1996; 59(1) :67-74 (Exhibit 38).
Imai K and D'Armiento J: Activation of an Embryonic Gene Product in Pulmonary Emphysema: identification of the xecreted frizzled-related protein. Chest May 2000; 117 (5 Suppl 1) :229S (Exhibit 39).
U.S. Appl. No. 09/514,885, filed Feb. 29, 2000 (Exhibit 40).

* cited by examiner

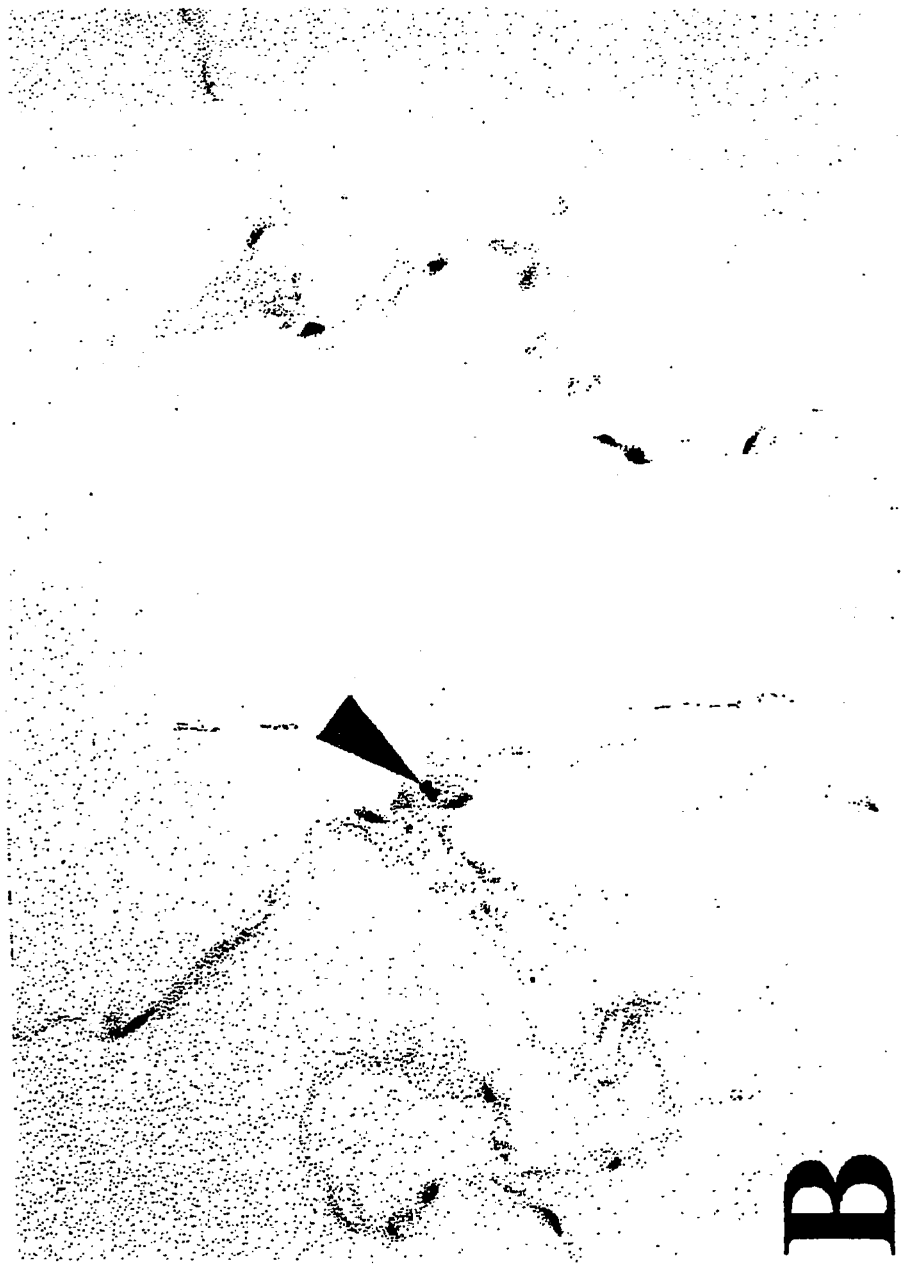
FIGURE IB

| Grade | Surface Area ($mm^2$) | Apoptotic Index (%) |
|---|---|---|
| Normal-Mild | 179.8 ± 43.3 | 1.1 ± 1.4 |
| Moderate-Severe | 66.7 ± 18.9 | 7.5 ± 3.2 |

Emp 1 Emp 2 Nor 1 Nor 2

I-41

I-41

Annexin/s Frp1
Casp3/sFrp1
Annexin/Gfp
A
B
C
D
E
F
SAEC
HMVEC

SEQUENCE LISTING

```
<160> NUMBER OF SEQ ID NOS: 38

<210> SEQ ID NO 1
<211> LENGTH: 313
<212> TYPE: PRT
<213> ORGANISM: Homo Sapiens

<400> SEQUENCE: 1

Met Gly Ile Gly Arg Ser Glu Gly Gly Arg Arg Gly Ala Leu Gly Val
1               5                   10                  15

Leu Leu Ala Leu Gly Ala Ala Leu Leu Ala Val Gly Ser Ala Ser Glu
            20                  25                  30

Tyr Asp Tyr Val Ser Phe Gln Ser Asp Ile Gly Pro Tyr Gln Ser Gly
        35                  40                  45

Arg Phe Tyr Thr Lys Pro Pro Gln Cys Val Asp Ile Pro Ala Asp Leu
    50                  55                  60

Arg Leu Cys His Asn Val Gly Tyr Lys Lys Met Val Leu Pro Asn Leu
65                  70                  75                  80

Leu Glu His Glu Thr Met Ala Glu Val Lys Gln Gln Ala Ser Ser Trp
                85                  90                  95

Val Pro Leu Leu Asn Lys Asn Cys His Ala Gly Thr Gln Val Phe Leu
            100                 105                 110

Cys Ser Leu Phe Ala Pro Val Cys Leu Asp Arg Pro Ile Tyr Pro Cys
        115                 120                 125

Arg Trp Leu Cys Glu Ala Val Arg Asp Ser Cys Glu Pro Val Met Gln
    130                 135                 140

Phe Phe Gly Phe Tyr Trp Pro Glu Met Leu Lys Cys Asp Lys Phe Pro
145                 150                 155                 160

Glu Gly Asp Val Cys Ile Ala Met Thr Pro Pro Asn Ala Thr Glu Ala
                165                 170                 175

Ser Lys Pro Gln Gly Thr Thr Val Cys Pro Pro Cys Asp Asn Glu Leu
            180                 185                 190

Lys Ser Glu Ala Ile Ile Glu His Leu Cys Ala Ser Glu Phe Ala Leu
        195                 200                 205

Arg Met Lys Ile Lys Glu Val Lys Lys Glu Asn Gly Asp Lys Lys Ile
    210                 215                 220

Val Pro Lys Lys Lys Lys Pro Leu Lys Leu Gly Pro Ile Lys Lys Lys
225                 230                 235                 240

Asp Leu Lys Lys Leu Val Leu Tyr Leu Lys Asn Gly Ala Asp Cys Pro
                245                 250                 255

Cys His Gln Leu Asp Asn Leu Ser His His Phe Leu Ile Met Gly Arg
            260                 265                 270

Lys Val Lys Ser Gln Tyr Leu Leu Thr Ala Ile His Lys Trp Asp Lys
        275                 280                 285

Lys Asn Lys Glu Phe Lys Asn Phe Met Lys Lys Met Lys Asn His Glu
    290                 295                 300

Cys Pro Thr Phe Gln Ser Val Phe Lys
305                 310


<210> SEQ ID NO 2
<211> LENGTH: 2075
<212> TYPE: DNA
<213> ORGANISM: Homo Sapiens
```

-continued

<400> SEQUENCE: 2

```
cctgcagcct ccggagtcag tgccgcgcgc ccgccgcccc gcgccttcct gctcgccgca     60

cctccgggag ccggggcgca cccagcccgc agcgccgcct ccccgcccgc gccgcctccg    120

accgcaggcc gagggccgcc actggccggg gggaccgggc agcagcttgc ggccgcggag    180

ccgggcaacg ctggggactg cgccttttgt ccccggaggt ccctggaagt ttgcggcagg    240

acgcgcgcgg ggaggcggcg gaggcagccc cgacgtcgcg gagaacaggg cgcagagccg    300

gcatgggcat cgggcgcagc gaggggggcc gccgcggggc cctgggcgtg ctgctggcgc    360

tgggcgcggc gcttctggcc gtgggctcgg ccagcgagta cgactacgtg agcttccagt    420

cggacatcgg cccgtaccag agcgggcgct tctacaccaa gccacctcag tgcgtggaca    480

tccccgcgga cctgcggctg tgccacaacg tgggctacaa gaagatggtg ctgcccaacc    540

tgctggagca cgagaccatg gcggaggtga agcagcaggc cagcagctgg gtgcccctgc    600

tcaacaagaa ctgccacgcc gggacccagg tcttcctctg ctcgctcttc gcgcccgtct    660

gcctggaccg gcccatctac ccgtgtcgct ggctctgcga ggccgtgcgc gactcgtgcg    720

agccggtcat gcagttcttc ggcttctact ggcccgagat gcttaagtgt gacaagttcc    780

cggagggga cgtctgcatc gccatgacgc cgcccaatgc caccgaagcc tccaagcccc    840

aaggcacaac ggtgtgtcct ccctgtgaca acgagttgaa atctgaggcc atcattgaac    900

atctctgtgc cagcgagttt gcactgagga tgaaaataaa agaagtgaaa aaagaaaatg    960

gcgacaagaa gattgtcccc aagaagaaga agcccctgaa gttggggccc atcaagaaga   1020

aggacctgaa gaagcttgtg ctgtacctga agaatggggc tgactgtccc tgccaccagc   1080

tggacaacct cagccaccac ttcctcatca tgggccgcaa ggtgaagagc cagtacttgc   1140

tgacggccat ccacaagtgg gacaagaaaa acaaggagtt caaaaacttc atgaagaaaa   1200

tgaaaaacca tgagtgcccc acctttcagt ccgtgtttaa gtgattctcc cgggggcagg   1260

gtggggaggg agcctcgggt ggggtgggag cggggggac agtgcccggg aacccgtggt    1320

cacacacacg cactgccctg tcagtagtgg acattgtaat ccagtcggct tgttcttgca   1380

gcattcccgc tccctttccc tccatagcca cgctccaaac cccagggtag ccatggccgg   1440

gtaaagcaag ggccatttag attaggaagg tttttaagat ccgcaatgtg gagcagcagc   1500

cactgcacag gaggaggtga caaaccattt ccaacagcaa cacagccact aaaacacaaa   1560

aaggggatt gggcggaaag tgagagccag cagcaaaaac tacattttgc aacttgttgg    1620

tgtggatcta ttggctgatc tatgcctttc aactagaaaa ttctaatgat tggcaagtca   1680

cgttgttttc aggtccagag tagtttcttt ctgtctgctt taaatggaaa cagactcata   1740

ccacacttac aattaaggtc aagcccagaa agtgataagt gcagggagga aaagtgcaag   1800

tccattatct aatagtgaca gcaaagggac caggggagag gcattgcctt ctctgcccac   1860

agtctttccg tgtgattgtc tttgaatctg aatcagccag tctcagatgc cccaaagttt   1920

cggttcctat gagcccgggg catgatctga tccccaagac atgtggaggg gcagcctgtg   1980

cctgcctttg tgtcagaaaa aggaaaccac agtgagcctg agagagacgg cgattttcgg   2040

gctgagaagg cagtagtttt caaaacacat agtta                              2075
```

<210> SEQ ID NO 3
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 3
tacaagaaga tggtgctgcc 20

<210> SEQ ID NO 4
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 4
agcacaagct tcttcaggtc 20

<210> SEQ ID NO 5
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 5
agatgttcaa tgatggcctc 20

<210> SEQ ID NO 6
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 6
tcttcctctt tggccagccc 20

<210> SEQ ID NO 7
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 7
tcacatcaat ttggagcttc 20

<210> SEQ ID NO 8
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 8
tctgcaccat tgacttccag 20

<210> SEQ ID NO 9
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 9
tctcagctat agagccttcc 20

-continued

```
<210> SEQ ID NO 10
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 10

ttagaatctc cttcacctcc                                                   20


<210> SEQ ID NO 11
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 11

gatgaggact tgaagatctc                                                   20


<210> SEQ ID NO 12
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 12

tcctggccat cgagcagtac                                                   20


<210> SEQ ID NO 13
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 13

actcggatac gcaggtcttc                                                   20


<210> SEQ ID NO 14
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 14

ttcttgtccc agcggtagac                                                   20


<210> SEQ ID NO 15
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 15

tcctccacga acctgcttac                                                   20


<210> SEQ ID NO 16
<211> LENGTH: 20
<212> TYPE: DNA
<213> ORGANISM: Artificial Sequence
<220> FEATURE:
<223> OTHER INFORMATION: Primer for Fizzeled Gene
```

-continued

<400> SEQUENCE: 16
acatcccgtg gcacttgcac 20

<210> SEQ ID NO 17
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 17
ttcgatggaa ccttctgagc 20

<210> SEQ ID NO 18
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 18
gacagaagaa actgtgccac 20

<210> SEQ ID NO 19
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 19
tgtcttcagg ctacatgagc 20

<210> SEQ ID NO 20
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 20
cgcaagtatc agtttgcctg 20

<210> SEQ ID NO 21
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 21
tagagatgga gcgaaaggtg 20

<210> SEQ ID NO 22
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 22
tggtacttct ccttcaggtg 20

-continued

```
<210> SEQ ID NO 23
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 23

tctcagctac aagtttctgg                                                20


<210> SEQ ID NO 24
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 24

ccatgctgaa gaagtagagc                                                20


<210> SEQ ID NO 25
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 25

tgtgctacaa cgtctactcg                                                20


<210> SEQ ID NO 26
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 26

atgagcttct ccagcttctc                                                20


<210> SEQ ID NO 27
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 27

tcctatgcac tatgtacacg                                                20


<210> SEQ ID NO 28
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 28

tgtccatgtc gatgaggaag                                                20


<210> SEQ ID NO 29
<211> LENGTH: 20
<212> TYPE: DNA
<213> ORGANISM: Artificial Sequence
<220> FEATURE:
<223> OTHER INFORMATION: Primer for Fizzeled Gene
```

-continued

<400> SEQUENCE: 29
tggattttgg tgtccaaggc 20

<210> SEQ ID NO 30
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 30
aagaatcacc caccacacag 20

<210> SEQ ID NO 31
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 31
ttccacccat ggcaaattcc 20

<210> SEQ ID NO 32
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 32
tttctagacg gcaggtcagg 20

<210> SEQ ID NO 33
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 33
agcgacgtgc aaaaggagag 20

<210> SEQ ID NO 34
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 34
agcctgaaat gcctcatgtc 20

<210> SEQ ID NO 35
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 35
acatgaccaa gatgcccaac 20

-continued

```
<210> SEQ ID NO 36
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 36

tcccttggaa tgtttaccag                                              20


<210> SEQ ID NO 37
<211> LENGTH: 20
<212> TYPE: DNA
<213> ORGANISM: Artificial Sequence
<220> FEATURE:
<223> OTHER INFORMATION: Primer for Fizzeled Gene

<400> SEQUENCE: 37

atgcatcctg taccaccaac                                              20


<210> SEQ ID NO 38
<211> LENGTH: 20
<212> TYPE: DNA
<213> ORGANISM: Artificial Sequence
<220> FEATURE:
<223> OTHER INFORMATION: Primer for Fizzeled gene

<400> SEQUENCE: 38

tggtcctctg tgtaagcaag                                              20
```

THERAPEUTIC TREATMENT OF CHRONIC OBSTRUCTIVE PULMONARY DISEASE

This application is a continuation-in-part of U.S. Ser. No. 09/514,885, filed Feb. 29, 2000, now U.S. Pat. No. 6,656, 461 the contents of which are hereby incorporated by reference.

Throughout this application, various publications are cited by reference numbers. Full citations for these publications may be found listed at the end of the specification immediately preceding the claims. Certain references and publications are cited by full citation. The disclosures of these publications in their entireties are hereby incorporated by reference into this application in order to more fully describe the state of the art as known to those skilled therein as of the date of the invention described and claimed herein.

BACKGROUND OF THE INVENTION

Chronic obstructive pulmonary disease (COPD), consisting of emphysema and chronic bronchitis, is the fourth leading cause of death in the United States(1). Approximately 15 million Americans are affected by COPD and there is an increasing incidence in women(2). Smoking is the major risk factor for COPD and accounts for over 90% of cases seen worldwide. Despite the importance of the disease, there are no specific therapies available to limit or prevent the slow, progressive, destructive changes observed in COPD(3).

Currently the major hypothesis for the pathogenesis of emphysema is the protease-antiprotease theory(4,5). This model suggests that an imbalance between the levels of extracellular matrix degrading enzymes and their respective inhibitors damage the connective tissue matrix components. of the lung. Studies over the past 30 years have demonstrated differences in the protease levels in the lung of patients with emphysema when compared to normal lung tissue(6). However, the molecular consequences of this finding have not been determined.

Although studies have demonstrated loss of the extracellular matrix in the lung of patients with emphysema, an investigation as to whether cell death contributes to the pathogenesis of this disease has not been performed.

SUMMARY OF THE INVENTION

The present invention provides a method of treating or preventing a chronic obstructive pulmonary disease in a subject, comprising administering to said subject an amount of an agent effective to inhibit apoptosis of the subject's lung cells and thus treat or prevent chronic obstructive pulmonary disease in the subject. The present invention provides for a method of identifying a compound effective to treat or prevent a chronic obstructive pulmonary disease, comprising (a) contacting lung cells from a subject having a chronic obstructive pulmonary disease with the compound and measuring the level of apoptosis of the lung cells in the presence of said compound, (b) measuring the level of apoptosis of the lung cells from the same subject in the absence of said compound, (c) comparing the level of apoptosis in step (a) with the level of apoptosis in step (b), wherein a higher level of apoptosis in step (b) indicate that the compound is effective to treat or prevent chronic obstructive pulmonary disease.

Figure 1A:
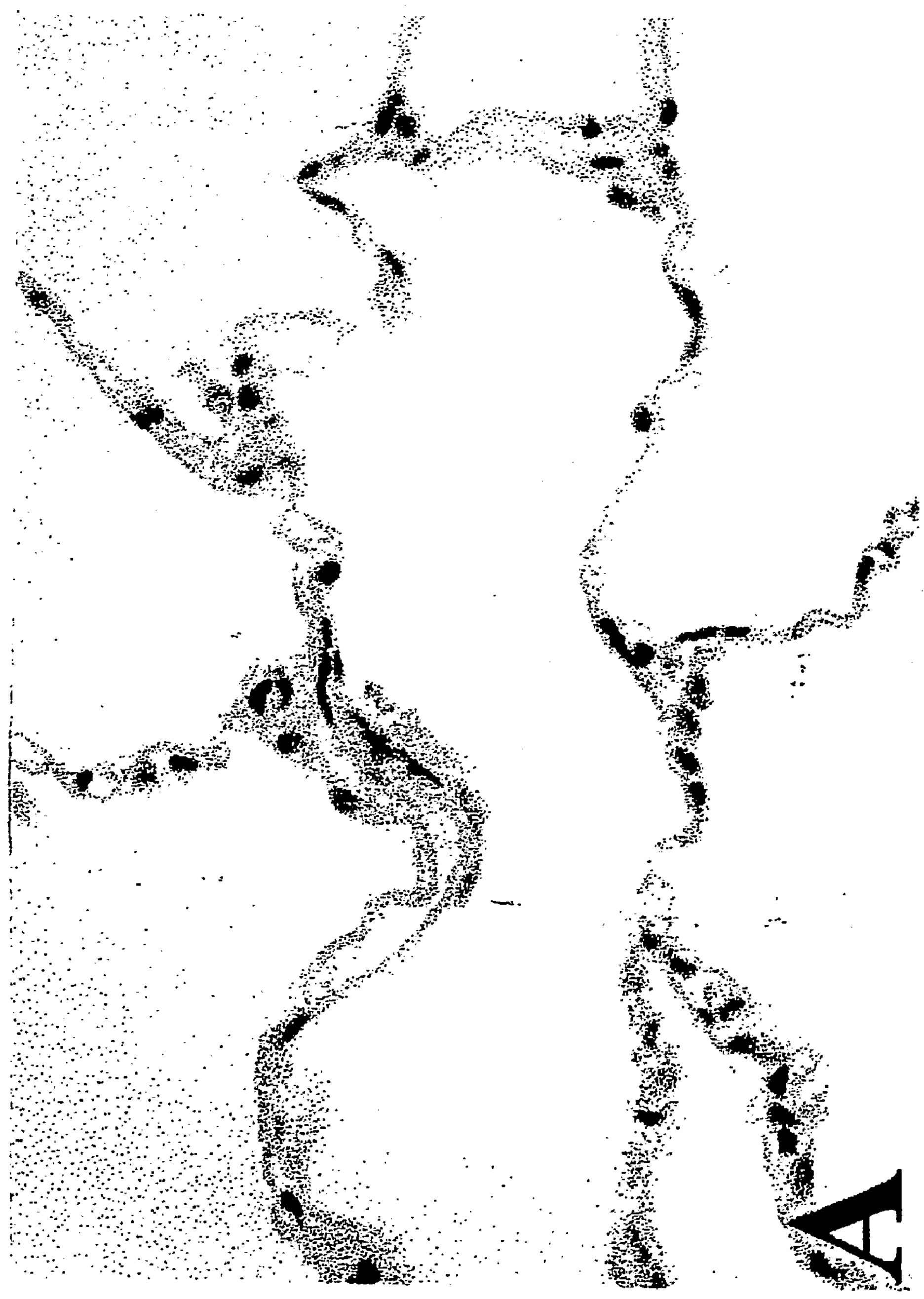
FIG. 1. Light micrographs and TUNNEL staining of normal and emphysema lungs.

Panels A and B show hematoxylin and eosin staining of a normal lung (A) and the lung from an emphysema patient (B). The emphysema lung exhibits thinning of the alveolar wall, and a pronounced hypocellularity. The arrowhead identifies the nuclear pyknosis and fragmentation. In panel C-E, the TUNNEL reaction with fluorescein-incorporated dUTP was specifically observed in the emphysema lung specimen (D), but not in the normal counterpart (C). Panel E represents the reaction without TdT in the emphysema lung. The TUNNEL reaction with biotinylated dUTP localizes apoptotic cells to both the alveolar surface and mesenchyme of the emphysema lung (G). Note some macrophage-like cells contain TUNEL-reactive material in their cytoplasm (inset) The normal lung was not stained (F). Bar: 50 μm (A, B, F and G), 100 μm (C-E) and 10 μm (inset in G).

Figure 2A:
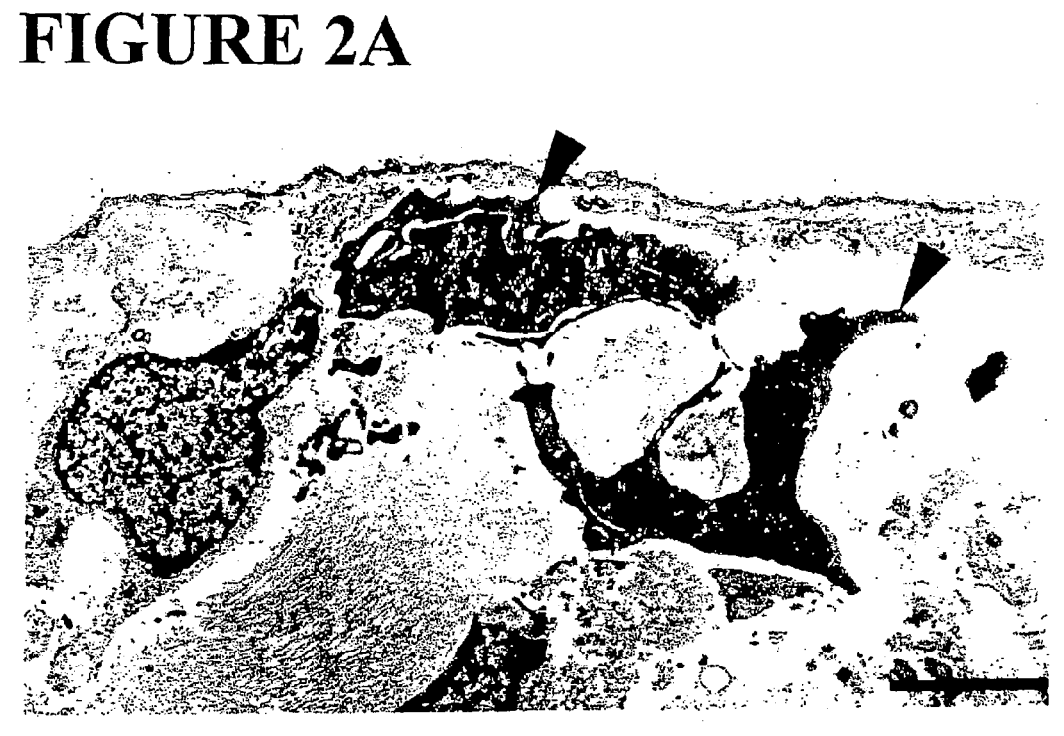

FIG. 2. Nuclear disruption in the emphysema lung samples.

A. Ultrastructure of the alveolar septum of the emphysema lung tissue. Apoptotic cells (arrowhead) adjacent to a normal cell (*) illustrate cytoplasmic condensation and shrinkage, with condensation of the nuclear chromatin. Loss of cell-extracellular matrix contact is also observed. Bar=2 μm. B. Isolated DNA from normal or emphysema lung tissues are electrophoresed on agarose gel (30 μg of DNA/lane) as described in the methods section. In contrast to high Mr intact DNA isolated from the normal lung samples (lanes 1-3), DNA from the emphysema lung samples shows a characteristic DNA laddering on the gel (lanes 4-7). Lane M indicates size of DNA by 1 kb ladder DNA marker.

FIG. 3. Morphometry and apoptotic index in lungs.

A. Surface area and apoptotic index in groups of normal or mild, and moderate to severe emphysema patients. A significant difference is seen between normal-mild and moderate-severe grades for surface area and apoptotic index ($p<0.01$). B. An inverse correlation between surface area and apoptotic index is observed by simple linear regression ($r2=0.605$).

FIG. 4. Caspase 3 and PARP cleavage in human lung tissue samples.

Tissue homogenates from normal (lanes 1-4) and emphysema lungs (lanes 5-8) were applied for the Western blot (120 g of total protein/lane) as described in METHODS. Lane 9 shows Jurkat cell lysates stimulated by anti-Fas antibody as a positive control. Expression of the pro-form of caspase 3 (32 kba) is recognized by a monoclonal antibody to caspase 3 in panel A. The active species of 17 and 12 kDa with a 24 kDa intermediate form are specifically detected by a rabbit polyclonal antibody in the emphysema samples (panel B). The degradation product of PARP at 85 kDa is observed in the emphysema lung samples but not in the normal lung samples (panel C).

FIG. 5. Detection of Bax and Bad and silver staining in lung samples.

Normal (A, C and E) and emphysema lung specimens (B, D and F) are subjected to immunostaining for Bcl-2 (A and B), Bax (C and D) and Bad (E and F). In the emphysema samples Bax is immunolocalized to the alveolar surface epithelial cells (arrowheads) (D), while both mesenchymal (arrow) and alveolar surface epithelial cells (arrowhead) are recognized by the antibody to Bad (F). A high power view in panel D inset demonstrates inclusion of anti-Bax antibody-reacted material in a macrophage-like cell. Bar: 50 μm (A, B, E and F), 25 μm (C and D) and 10 μm (inset in D).

FIG. 6. Identification of sFRP1 expression in human lungs.

A, Differential Display was carried out with an upstream arbitrary primer and a downstream anchor primer using total RNA samples isolated from emphysema (Emp 1 and 2) and normal lungs (Nor 1 and 2). The arrowhead indicates the band for clone 1-41 which is detectable in the emphysema but not normal lung samples. B, Cloned PCR fragments were screened by dot blot hybridization using $P^{32}$-labeled emphysema and normal lung first strand cDNA. The upper membrane was screened with the emphysema specific probe and demonstrated three positive clones including 1-41 (arrow). The lower membrane was hybridized with the normal lung probe. C, Total RNA isolated from emphysema (Emp 1-4) and normal lungs (Nor 5-9) was subjected to RT-PCR using specific primers for sFRP1, 2 and 3, respectively. No-RT is without reverse transcriptase in sample Emp 2. Exclusive amplification of sFRP1 in the emphysema samples was observed. As an internal control for the presence of mRNA, RT-PCR was performed using a primer set for human GAPDH.

Figure 7:
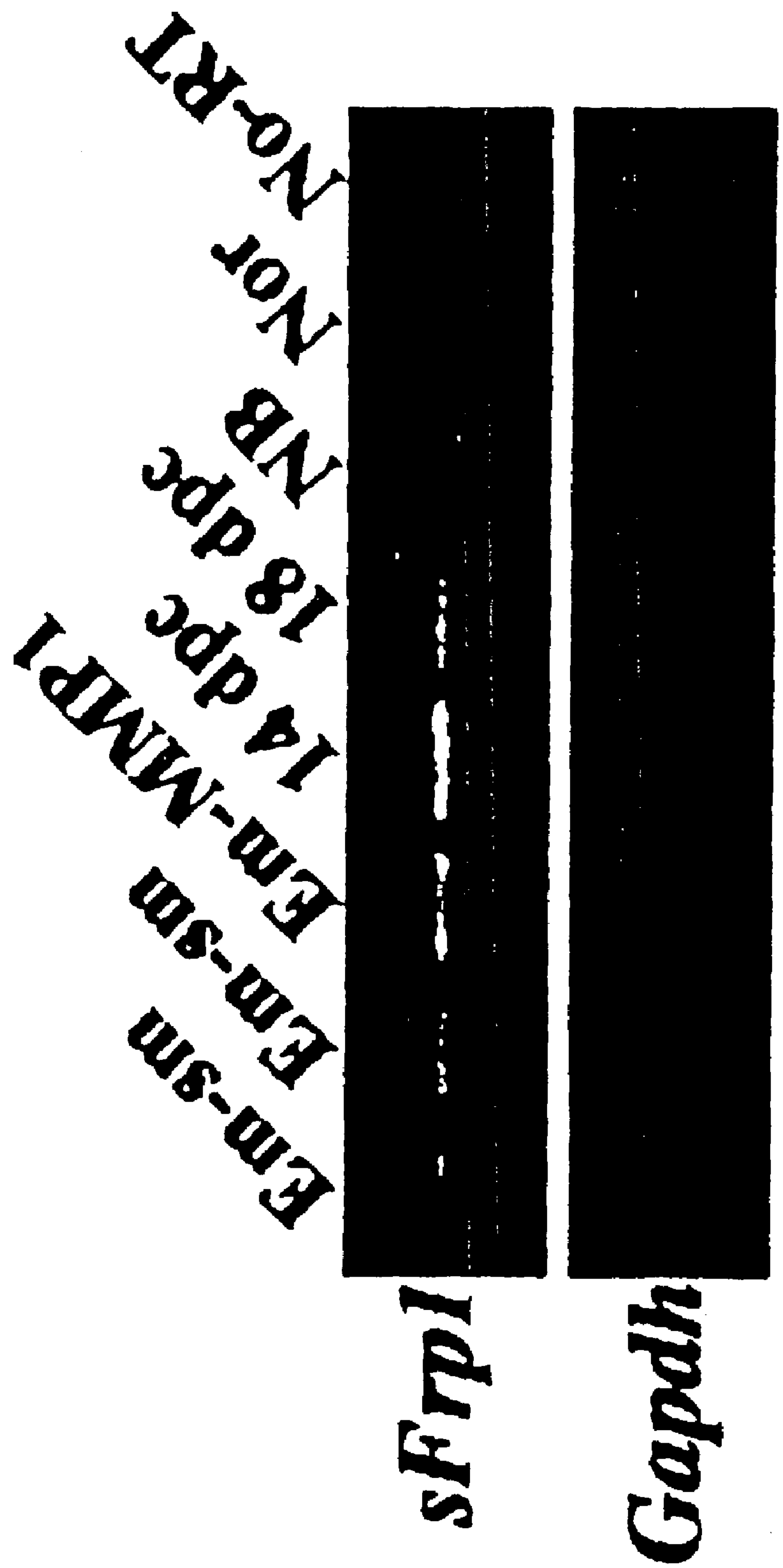

FIG. 7. sFrp1 expression in mouse lungs.

RT-PCR was undertaken for mouse samples. Mouse lung total RNA was isolated from. cigarette-exposed (Em-sm) and collagenase transgenic mice (Em-MMPl), 14 dpc and 18 dpc embryo, newborn (NB) and normal adult mice (Nor). A reaction without reverse transcriptase in samples Em-MMPl is represented in the No-RT lane. Note sFrp1 expression in the emphysema mouse models (Em-sm and Em-MMPl) and embryos (14 and 18 dpc). As an internal control for the presence of mRNA, RT-PCR was performed using a primer set for mouse Gapdh.

Figure 8:
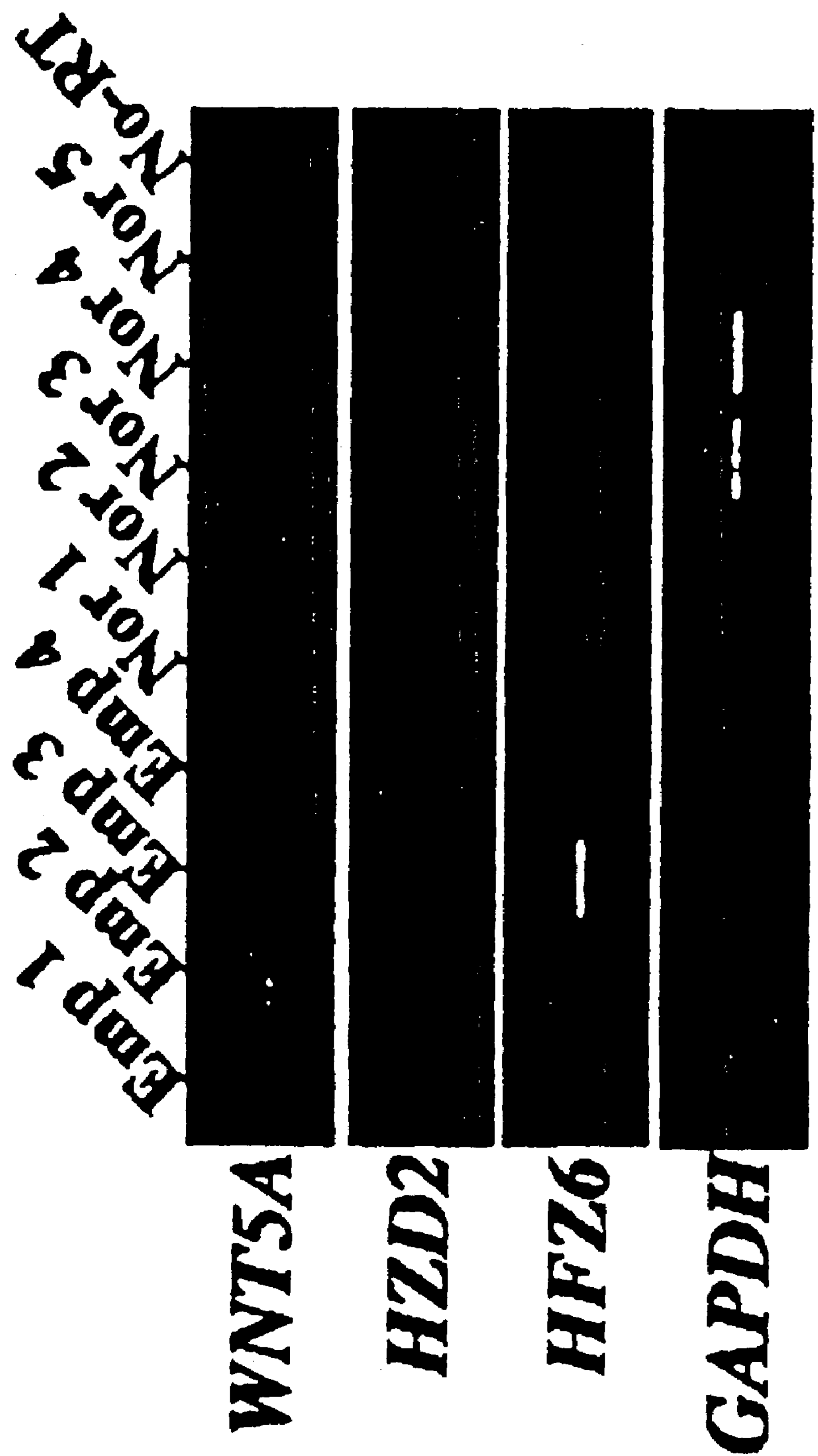

FIG. 8. RT-PCR amplification of WNT and FZ mRNA in human lung.

Emphysema (Emp 1-4) and normal lung RNA (Nor5-9) were reverse transcribed by Superscript II using random oligomer. Primer pairs specific for WNT5A, HZD2, HFZ6 and GAPDH were used for the PCR reaction.

Figure 9:
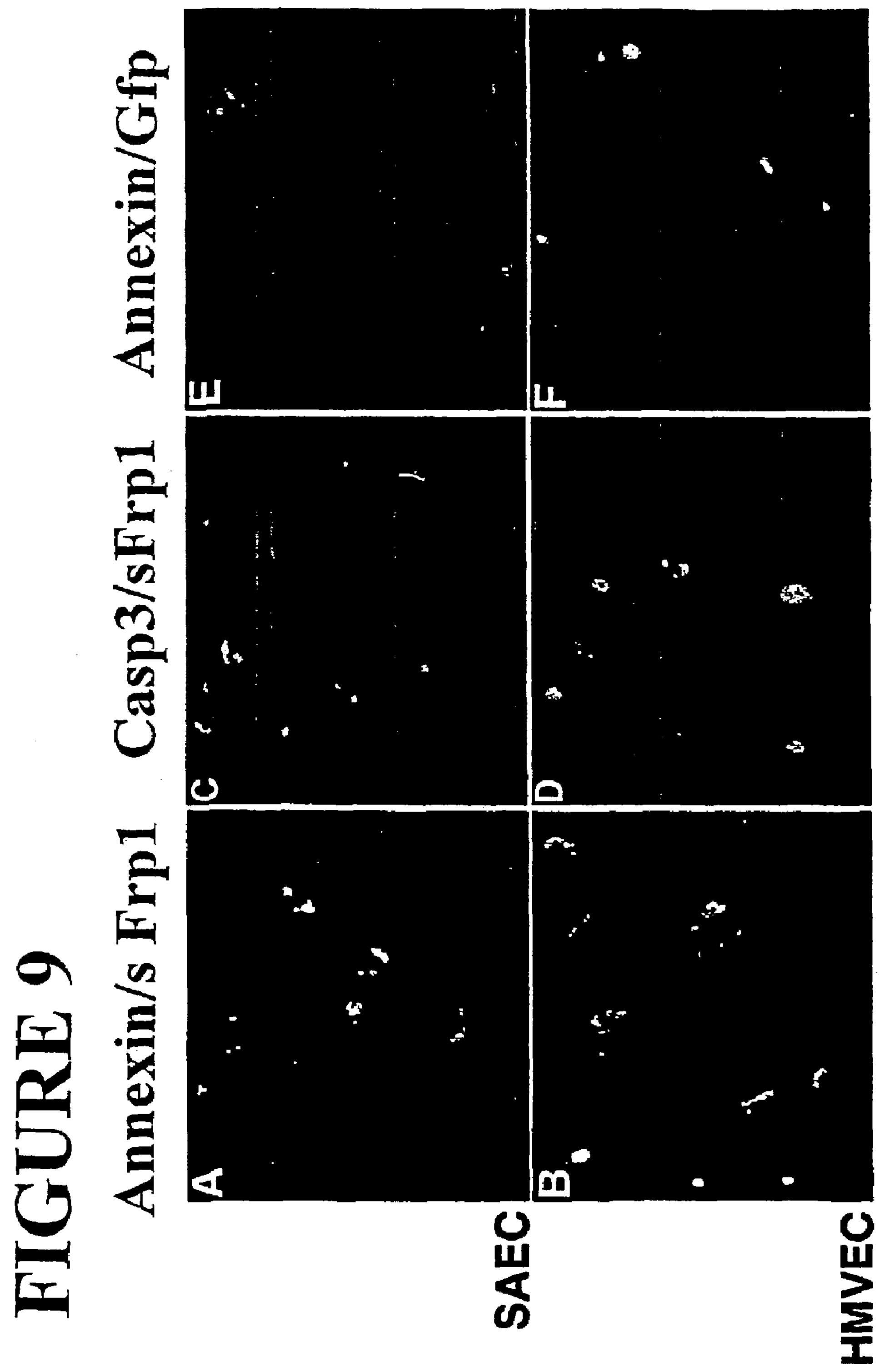

FIG. 9. SFRP-1 leads to apoptosis of lung epithelial, endothelial & fibroblast cells in vitro.

DETAILED DESCRIPTION OF THE INVENTION

The present invention provides a method of treating or preventing a chronic obstructive pulmonary disease in a subject, comprising administering to said subject an amount of an agent effective to inhibit apoptosis of the subject's lung cells and thus treat or prevent chronic obstructive pulmonary disease in the subject.

In one embodiment, the agent inhibits apoptosis by inhibiting an apoptotic pathway. In another embodiment of the invention, the agent inhibits the apoptotic pathway by inhibiting expression of the sFRP gene.

In another embodiment of the invention, the sFRP gene comprises a nucleic acid molecule comprising nucleotides having the sequence set forth in SEQ ID NO:1.

In another embodiment of the invention, the chronic obstructive pulmonary disease is emphysema.

In another embodiment of the invention, the chronic obstructive pulmonary disease is chronic bronchitis.

In another embodiment of the invention, the agent is selected from a group consisting of an antisense molecule, a b chemokine, and a plant-derived composition.

In another embodiment of the invention, the antisense molecule comprises nucleic acid having 8-30 nucleotides.

In another embodiment of the invention, the b chemokine is b chemokine I-309.

In another embodiment of the invention, the b chemokine is b chemokine TCA-3.

In another embodiment of the invention, the agent is the Herpes simplex virus ICP4.

The present invention provides for a method of identifying a compound effective to treat or prevent a chronic obstructive pulmonary disease, comprising (a) contacting lung cells from a subject having a chronic obstructive pulmonary disease with the compound and measuring the level of apoptosis of the lung cells in the presence of said compound, (b) measuring the level of apoptosis of the lung cells from the same subject in the absence of said compound, (c) comparing the level of apoptosis in step (a) with the level of apoptosis in step (b), wherein a higher level of apoptosis in step (b) indicate that the compound is effective to treat or prevent chronic obstructive pulmonary disease.

In another embodiment of the invention, the level of apoptosis is determined by measuring DNA fragmentation or cleavage.

In another embodiment of the invention, the level of apoptosis is determined by measuring the expression of activated caspase 3.

In another embodiment of the invention, the level of apoptosis is determined by measuring the presence of poly (ADP ribose) polymerase.

In another embodiment of the invention, the level of apoptosis is determined by morphometric analysis.

In another embodiment of the invention, the level of apoptosis is determined by measuring Bcl-2 and Bad expression.

The invention also provides a method of treating or preventing a chronic obstructive pulmonary disease in a subject, comprising administering to the subject an amount of an agent effective to inhibit expression of a secreted Frizzled-related protein (sFRP) gene of the subject's lung cells and thus treat or prevent chronic obstructive pulmonary disease in the subject. The chronic obstructive pulmonary disease may be emphysema or chronic bronchitis.

The invention also provides an antibody capable of specifically binding to sFRP, more specifically to sFRP-1. The antibody may be a monoclonal antibody or a polyclonal antibody. The antibody may be humanized.

The antibody may also be detectable. The antibody may be made detectable by being labeled with a detectable marker. The the detectable marker may be is a radioactive label or a calorimetric, or a luminescent, or a fluorescent marker.

The invention also provides a composition comprising the antibody and an agent conjugated to the antibody. The agent may be a radioactive isotope or toxin.

The invention also provides a method of determining whether a subject is afflicted with a chronic obstructive pulmonary disease which comprises: (a) obtaining a suitable sample from the subject; (b) contacting the suitable sample with the detectable antibody of claim 16 so as to form a complex between the antibody and sFRP or fragment thereof present in the sample; (c) removing any unbound antibody; and (d) detecting any antibody which is bound to any sFRP in the sample, wherein the presence of antibody indicates that the subject is afflicted with the chronic obstructive pulmonary disease. The disiease may be emphysema. The suitable sample may be lung tissue.

In the method, the antigen bound by the antibody is detected by an immunoassay. The immunoassay may be ELISA, IFA, or Western blotting.

The invention also provides a kit for diagnosing chronic obstructive pulmonary disease comprising the labeled antibody. The kit may furthe comprise a means for determining the level of sFRP or fragment thereof bound by an antibody. In the kit, the antibody may be bound to a support.

The invention also provides a method of inhibiting sFRP mediated apoptosis of a cell which comprises introducing into the cell an effective amount of the replicable vector which expresses an antisense molecule to the gene encoding sFRP so as to thereby inhibit sFRP mediated apoptosis of the cell. The sFRP may be sFRP-1.

The invention also provides a method for evaluating in a non-human transgenic animal the potential therapeutic effect of an agent for treating chronic obstructive pulmonary disease in a human, which comprises: (a) providing an agent to a transgenic non-human animal having chronic obstructive pulmonary disease;(b) determining the therapeutic effect of the agent on the transgenic non-human animal by monitoring sFRP expression, wherein a decrease in sFRP indicates that the agent would have a potential therapeutic effect on chronic obstructive pulmonary disease in a human. The animal may be a mammal. The non-human animal may be a mouse, a rat, a sheep, a dog, a primate, or a reptile.

The invention also provides method of detecting a chronic obstr a) obtaining a suitable sample of mRNA from the subject; b) contacting the mRNA sample under hybridizing conditions with a labeled nucleic acid probe which: (1) is at least 15 nucleotides in length and (2) hybridizes specifically to a nucleic acid having a sequence which is complementary to a sequence present in the sequence set forth in SEQ ID NO. 2; c) removing any unbound labeled nucleic acid probe; and d) detecting the presence of labeled nucleic acid probe hybridized to the mRNA so as to thereby detect chronic obstructive pulmonary disease in the subject.

In the method, the mRNA may be from lung tissue of the subject.

The invention also provides method of detecting chronic obstructive pulmonary disease in a subject which comprises: a) obtaining a suitable sample of mRNA from the subject; b) reverse transcribing the mRNA to generate a single-stranded cDNA; c) contacting the single-stranded cDNA under hybridizing conditions with a labeled nucleic acid probe which: 1) is at least 15 nucleotides in length; and 2) hybridizes specifically to a nucleic acid having a sequence set forth in SEQ ID NO:2; d) removing any unbound labeled nucleic acid probe; and e) detecting the presence of labeled nucleic acid probe hybridized to the cDNA so as to thereby detect detect chronic obstructive pulmonary disease in the subject.

The invention also provides method of detecting chronic obstructive pulmonary disease in a subject which comprises: a) obtaining a suitable sample of mRNA from the subject;

b) generating a double-stranded mRNA-cDNA duplex from the mRNA; c) contacting the duplex from (b) with one primer having a sequence which is complementary to a portion of the sequence set forth in SEQ ID NO:2 and a second primer having a sequence which comprises a different portion of the sequence set forth in SEQ ID NO:2; d) amplifying the nucleic acid from (c) using a polymerase chain reaction to obtain an amplification product; e) contacting the amplification product of (d) under hybridizing conditions with a labeled nucleic acid probe which: 1) is at least 15 nucleotides in length; 2) hybridizes specifically to a nucleic acid having a sequence set forth in SEQ ID NO. 2; f) removing any unbound labeled nucleic acid probe; and g) detecting the presence of labeled nucleic acid probe hybridized to the amplification product so as to thereby detect chronic obstructive pulmonary disease in the subject.

As used herein, the term "apoptosis" means programmed cell death or cell death caused by an active process of gene-directed cellular self-destruction and characterized by the rapid condensation of the cell with preservation of membranes, the compaction of chromatin, and DNA cleavage and fragmentation. The mechanism of apoptosis is described in detail in Granville D. J., et al. (1998) "Apoptosis: Molecular aspects of cell death and disease" Lab. Invest., 78:893-913 and the content of Granville D. J., et al. is fully incorporated in its entirety by reference.

As used herein, "Wnt gene" represents genes encoding Wnt glycoproteins which serve as inducers of cellular proliferation, migration, differentiation and tissue morphogenisis during normal development.

The term "FRP" means Frizzled-related Proteins which contain a region homologous to a putative Wnt-binding domain of Frizzleds and which serve as antagonists of Wnt action. The term "sFRP" means secreted Frizzled-related Proteins. EP 0 879 885 discusses a human gene similar to a secreted murine protein sFRP-1. One of the Frizzled-related Proteins or the secreted Frizzled-related Proteins is a polypeptide having an am

```
                                              (SEQ ID NO:1)
MGIGRSEGGRRGALGVLLALGAALLAVGSASEYDYVSFQSDIGPYQSGRF

YTKPPQCVDIPADLRLCHNVGYKKMVLPNLLEHETMAEVKQQASSWVPLL

NKNCHAGTQVFLCSLFAPVCLDRPIYPCRWLCEAVRDSCEPVMQFFGFYW

PEMLKCDKFPEGDVCIAMTPPNATEASKPQGTTVCPPCDNELKSEAIIEH

LCASEFALRMKIKEVKKENGDKKIVPKKKKPLKLGPIKKKDLKKLVLYLK

NGADCPCHQLDNLSHHFLIMGRKVKSQYLLTAIHKWDKKNKEFKNFMKKM

KNHECPTFQSVFK
```

The term "sFRP genes" means DNA molecules encoding Frizzled-related Proteins. One of the sFRP genes is a nucleic acid comprising nucleotides having the sequence as set forth in SEQ ID NO:2 as follows:

```
CCTGCAGCCT CCGGAGTCAG TGCCGCGCGC CCGCCGCCCC GCGCCTTCCT (SEQ ID NO:2)

GCTCGCCGCA CCTCCGGGAG CCGGGGCGCA CCCAGCCCGC AGCGCCGCCT

CCCCGCCCGC GCCGCCTCCG ACCGCAGGCC GAGGGCCGCC ACTGGCCGGG

GGGACCGGGC AGCAGCTTGC GGCCGCGGAG CCGGGCAACG CTGGGGACTG

CGCCTTTTGT CCCCGGAGGT CCCTGGAAGT TTGCGGCAGG ACGCGCGCGG
```

-continued

GGAGGCGGCG GAGGCAGCCC CGACGTCGCG GAGAACAGGG CGCAGAGCCG

GCATGGGCAT CGGGCGCAGC GAGGGGGGCC GCCGCGGGGC CCTGGGCGTG

CTGCTGGCGC TGGGCGCGGC GCTTCTGGCC GTGGGCTCGG CCAGCGAGTA

CGACTACGTG AGCTTCCAGT CGGACATCGG CCCGTACCAG AGCGGGCGCT

TCTACACCAA GCCACCTCAG TGCGTGGACA TCCCCGCGGA CCTGCGGCTG

TGCCACAACG TGGGCTACAA GAAGATGGTG CTGCCCAACC TGCTGGAGCA

CGAGACCATG GCGGAGGTGA AGCAGCAGGC CAGCAGCTGG GTGCCCCTGC

TCAACAAGAA CTGCCACGCC GGGACCCAGG TCTTCCTCTG CTCGCTCTTC

GCGCCCGTCT GCCTGGACCG GCCCATCTAC CCGTGTCGCT GGCTCTGCGA

GGCCGTGCGC GACTCGTGCG AGCCGGTCAT GCAGTTCTTC GGCTTCTACT

GGCCCGAGAT GCTTAAGTGT GACAAGTTCC CGGAGGGGGA CGTCTGCATC

GCCATGACGC CGCCCAATGC CACCGAAGCC TCCAAGCCCC AAGGCACAAC

GGTGTGTCCT CCCTGTGACA ACGAGTTGAA ATCTGAGGCC ATCATTGAAC

ATCTCTGTGC CAGCGAGTTT GCACTGAGGA TGAAAATAAA AGAAGTGAAA

AAAGAAAATG GCGACAAGAA GATTGTCCCC AAGAAGAAGA AGCCCCTGAA

GTTGGGGCCC ATCAAGAAGA AGGACCTGAA GAAGCTTGTG CTGTACCTGA

AGAATGGGGC TGACTGTCCC TGCCACCAGC TGGACAACCT CAGCCACCAC

TTCCTCATCA TGGGCCGCAA GGTGAAGAGC CAGTACTTGC TGACGGCCAT

CCACAAGTGG GACAAGAAAA ACAAGGAGTT CAAAAACTTC ATGAAGAAAA

TGAAAAACCA TGAGTGCCCC ACCTTTCAGT CCGTGTTTAA GTGATTCTCC

CGGGGGCAGG GTGGGGAGGG AGCCTCGGGT GGGGTGGGAG CGGGGGGGAC

AGTGCCCGGG AACCCGTGGT CACACACACG CACTGCCCTG TCAGTAGTGG

ACATTGTAAT CCAGTCGGCT TGTTCTTGCA GCATTCCCGC TCCCTTTCCC

TCCATAGCCA CGCTCCAAAC CCCAGGGTAG CCATGGCCGG GTAAAGCAAG

GGCCATTTAG ATTAGGAAGG TTTTTAAGAT CCGCAATGTG GAGCAGCAGC

CACTGCACAG GAGGAGGTGA CAAACCATTT CCAACAGCAA CACAGCCACT

AAAACACAAA AAGGGGGATT GGGCGGAAAG TGAGAGCCAG CAGCAAAAAC

TACATTTTGC AACTTGTTGG TGTGGATCTA TTGGCTGATC TATGCCTTTC

AACTAGAAAA TTCTAATGAT TGGCAAGTCA CGTTGTTTTC AGGTCCAGAG

TAGTTTCTTT CTGTCTGCTT TAAATGGAAA CAGACTCATA CCACACTTAC

AATTAAGGTC AAGCCCAGAA AGTGATAAGT GCAGGGAGGA AAAGTGCAAG

TCCATTATCT AATAGTGACA GCAAAGGGAC CAGGGGAGAG GCATTGCCTT

CTCTGCCCAC AGTCTTTCCG TGTGATTGTC TTTGAATCTG AATCAGCCAG

TCTCAGATGC CCCAAAGTTT CGGTTCCTAT GAGCCCGGGG CATGATCTGA

TCCCCAAGAC ATGTGGAGGG GCAGCCTGTG CCTGCCTTTG TGTCAGAAAA

AGGAAACCAC AGTGAGCCTG AGAGAGACGG CGATTTTCGG GCTGAGAAGG

CAGTAGTTTT CAAAACACAT AGTTA

As used herein, the phrase "Chronic Obstructive Pulmonary Disease" means a process characterized by the presence of chronic bronchitis or emphysema that may lead to the development of airways obstruction, both reversible airways obstruction and irreversible airways obstruction. "Chronic obstructive pulmonary disease" includes chronic bronchitis, emphysema, and asthma.

As used herein, "inhibitors of cell apoptosis" includes, but not limited to, antisense compounds, such as described in Bennett, et al., U.S. Pat. No. 5,958,772, plant-derived compositions as described in Bathurst, et al., U.S. Pat. Nos. 5,620,885, 5,567,425, 5,624,672, 5,759,548 and 5,635,187, b chemokines, such as b chemokine I-309 and b chemokine TCA-3, as describe in Damme, et al., U.S. Pat. No. 5,824,551. "Inhibitors of cell apoptosis" also includes, but not limited to, and Herpes simplex virus ICP4 as described in Leopardi, et al., U.S. Pat. No. 5,876,923.

EXPERIMENTAL DETAILS

Example 1

Apoptosis in Human Emphysema Lungs, Implications for Novel Therapeutic Strategies Lung Samples: Human lung tissue was obtained between 1995-1999 from a total of 19 patients at Columbia Presbyterian Medical Center (IRB #X042 1) as follows: 14 samples were obtained from patients with emphysema who underwent lung transplant and five samples from patients who underwent lung volume reduction procedures. Samples from six normal lungs were used as controls. The six normal lung samples were obtained from donor lungs harvested from transplant but not used due to recipient complications or from accidental death victims. All of the emphysema samples were taken from patients who reportedly had stopped smoking for at least three months prior to harvesting the tissues. Cellular death was evaluated morphologically, histochemically and biochemically. Western blot analysis was performed to identify the presence of active caspase 3 and poly(ADP-ribose) polymerase in the emphysema tissue. Expression of the anti-apoptotic Bcl-2 protein, and its pro-apoptotic counterparts Bax and Bad were also determined through immunohistochemistry.

Histological Examination: After surgical excision, lungs were immediately fixed in 10% neutral buffered formalin for about 16 hours at 4° C. and embedded in paraffin-wax. Every sample was examined histologically in a blinded fashion for the presence of emphysema, fibrosis and inflammation and samples with pathological evidence of inflammation indicative of ongoing infection or neoplastic changes were excluded from this study. Sections (3 μm) were stained by silver impregnation for collagen fibrils(7,8). Immunohistochemical staining was performed using mouse IgG specific to human Bad (clone B31420, 10 g/ml) or Bcl-2 (clone B31420, 10 g/ml) (Transduction Laboratories, Lexington, Ky.) and rabbit polyclonal antibody to human Bax (clone 13666E, dilution×1,000. PharMingen, San Diego, Calif.). After incubation with biotinylated horse IgG to mouse IgG or goat IgG to rabbit IgG (Vector Laboratories, Burlingame, Calif.) and an avidin-biotin-peroxidase complex (DAKO, Glostrup, Denmark), color was developed with 3,3'-diaminobenzidine tetrahydrochloride. For transmission electron microscopy, tissues were cut into small pieces and fixed in 2.5% glutaraldehyde followed by 2% osmium tetroxide at 4° C. and processed to ultrathin sections for the electron microscope (1200 EX II, 80 KV, Jeol, Sundbyberg, Sweden).

In Situ Labeling of DNA Cleavage: Formalin-fixed specimens were subjected to oligonucleosomal fragment labeling of DNA by terminal deoxynucleotidyl transferase (TdT)-mediated X-dUTP nick end labeling (TUNNEL), using DeadEnd Colorimetric Apoptosis Detection System (Promega, Madison, Wis.) for streptavidin horseradish peroxidase-diaminobenzidine detection and In Situ Cell Death Detection Kit (Boehringer Mannheim, Indianapolis, Ind.) for fluorometric detection of apoptotic cells. These reactions were undertaken according to the manufacture's instructions. The percentage of TUNNEL reactive cells to total cells (apoptotic index) was measured in three different, areas in each specimen at 40-fold magnification using light microscopy. The significance of difference in the apoptotic index between normal-mild emphysema and moderate-severe emphysema was determined by a Mann-Whitney U test. As a positive control, lung specimens were treated with RNase-free DNase I (Boehringer Mannheim) followed by TdT reaction. As a negative control, TdT was omitted from the reactions.

Morphometric Analysis: Tissue sections were stained with hematoxylin and eosin and the mean linear intercept and internal surface area were calculated according to established methods (9-11) using a light microscope linked to a Macintosh computer and Adobe Photoshop imaging software. A rectangular grid of dots at approximately 1 mm intervals was applied to 10 different areas in each section. From a random starting position on the grid, sequential and spaced images were digitally recorded for analysis. A test system was randomly superimposed upon each image. Horizontal lines were used to count alveolar surface intersections. Endpoints were used to calculate alveolar volumes. Results were analyzed with one-way analysis of the variance and simple linea between surface area and apoptotic index.

DNA Fragmentation: Four emphysema and three normal lung tissues samples (100 mg of tissue wet weight) were digested with 0.1 mg/ml of Proteinase K for ~16 h in 1.2 ml of digestion buffer (10 mM Tris-HCl, 0.1 M NaCl, 25 mM EDTA, 0.5% SDS, pH 8.0). After protein extraction with phenol-chloroform isoamylalcohol and dialysis against 10 mM Tris-HCl, 1 mM EDTA, pH 8.0, samples were incubated with 1 μg/ml of RNase A for 1 h at 37° C. and dialyzed in 10 mM Tris-HCl, 1 mM EDTA, pH 8.0, at 4° C. For detection of DNA fragmentation, 30 μg of isolated DNA were size fractionated on 1.4% agarose gel containing 0.1 μg/ml of ethidium bromide.

Protein Preparation and Analysis: Tissue homogenates of six emphysema and five normal lungs were prepared in 20 mM Tris-HCl, pH 7.4, 0.15 M NaCl, 0.02% NaN3, 1% NP-40, 1 mM PMSF, 2 mM N-ethylmaleimide, 10 μg/ml of leupeptin, 1 μg/ml of aprotinin, 10 μg/ml of pepstatin A, 10 μM E-64 and 1 mM EDTA. Proteins (120 μg) in the homogenate was size fractionated on SDS-PAGE under reducing conditions and electrotransferred onto a nitrocellulose membrane (Trans-Blot, BioRad, Hercules, Calif.). For immunological detection of proteins, Western blot was performed using mouse IgG to human caspase 3, clone C31720, 0.4 μg/ml (Transduction Laboratories) or polyclonal rabbit anti-human caspase 3 (PharMingen, Clone 67341A, 1 μg/ml) as previously described (12). Rabbit antibody against the proteolytic fragment of poly(ADP-ribose) polymerase (PARP) (Promega, Clone G734, 0.35 μg/ml) was also used.

Fluorometric Assay: Four emphysema and four normal lung tissues were homogenized in 20 mM Tris-HCl, pH 7.4, 10 mM Na2P2O7, 100 mM NaF, 2 mM NaVO4, 5 mM EDTA, 1 mM PMSF, 10 μg/ml aprotinin, and 1% NP-40. After removal of insoluble materials, caspase 3 activity was quantified by the fluorometric assay using specific synthetic peptide substrate (Ac-DEVD-AMC, PharMingen) as previously described(13).

Morphological and Biochemical Detection of Apoptosis: In normal lungs, the alveolar wall consists of three tissue components including the surface epithelium, supporting connective tissue and blood vessels (FIG. 1A). The supporting tissue forms a layer beneath the epithelium and surrounding the blood vessels of the alveolar wall. In contrast, extensive loss of the alveolar architecture in the emphysema lungs is associated with hypocellularity and thinning of the remaining alveolar wall (FIG. 1B). Within the emphysema lung samples, cells were morphologically characteristic of cells undergoing apoptosis exhibiting convolution of nuclear outlines (FIG. 1B, arrow). These nuclear changes were observed in cells throughout the sample and not in focal regions as is seen in necrosis(14). The apoptotic cells included endothelial cells, epithelial cells and fibroblasts. Neutrophil infiltration into the alveolar space or the alveolar septa was negligible.

Figure 1C:
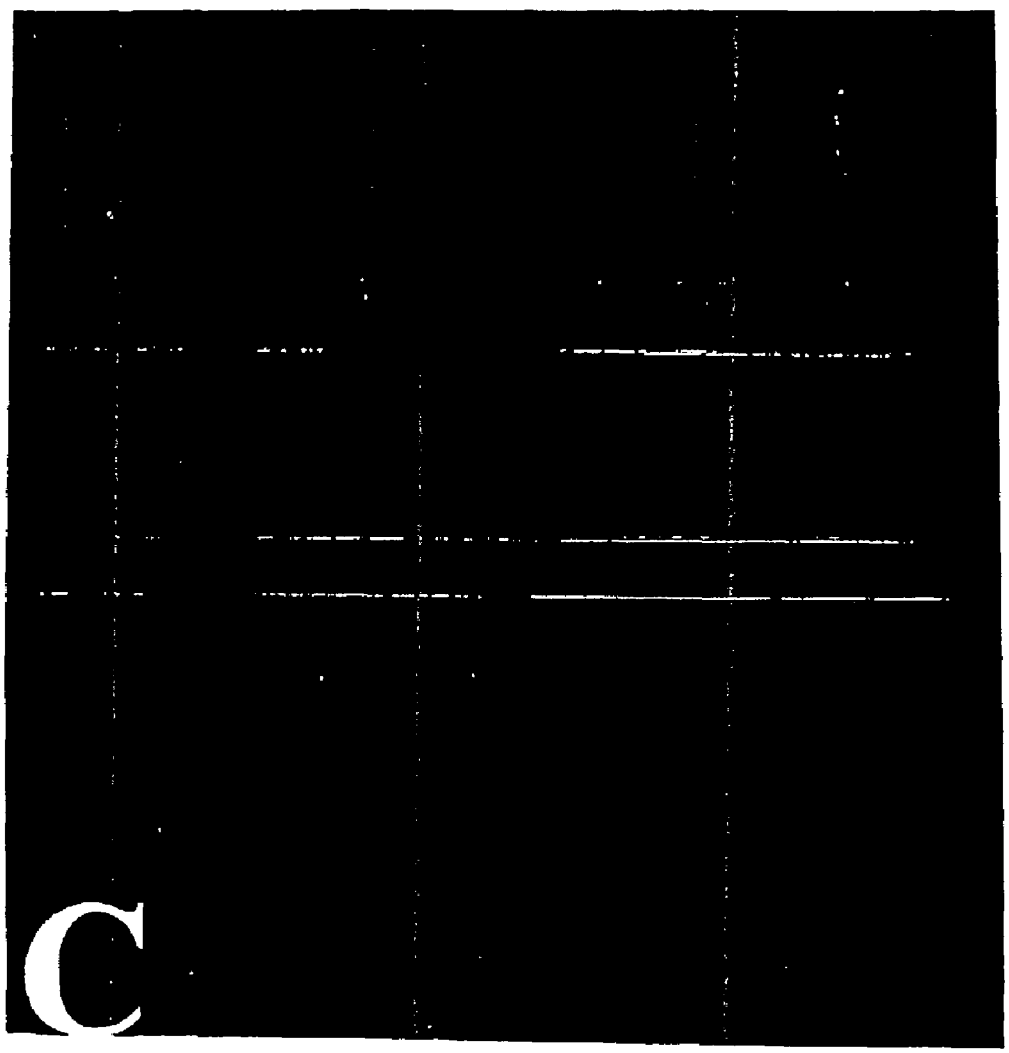
Figure 1D:
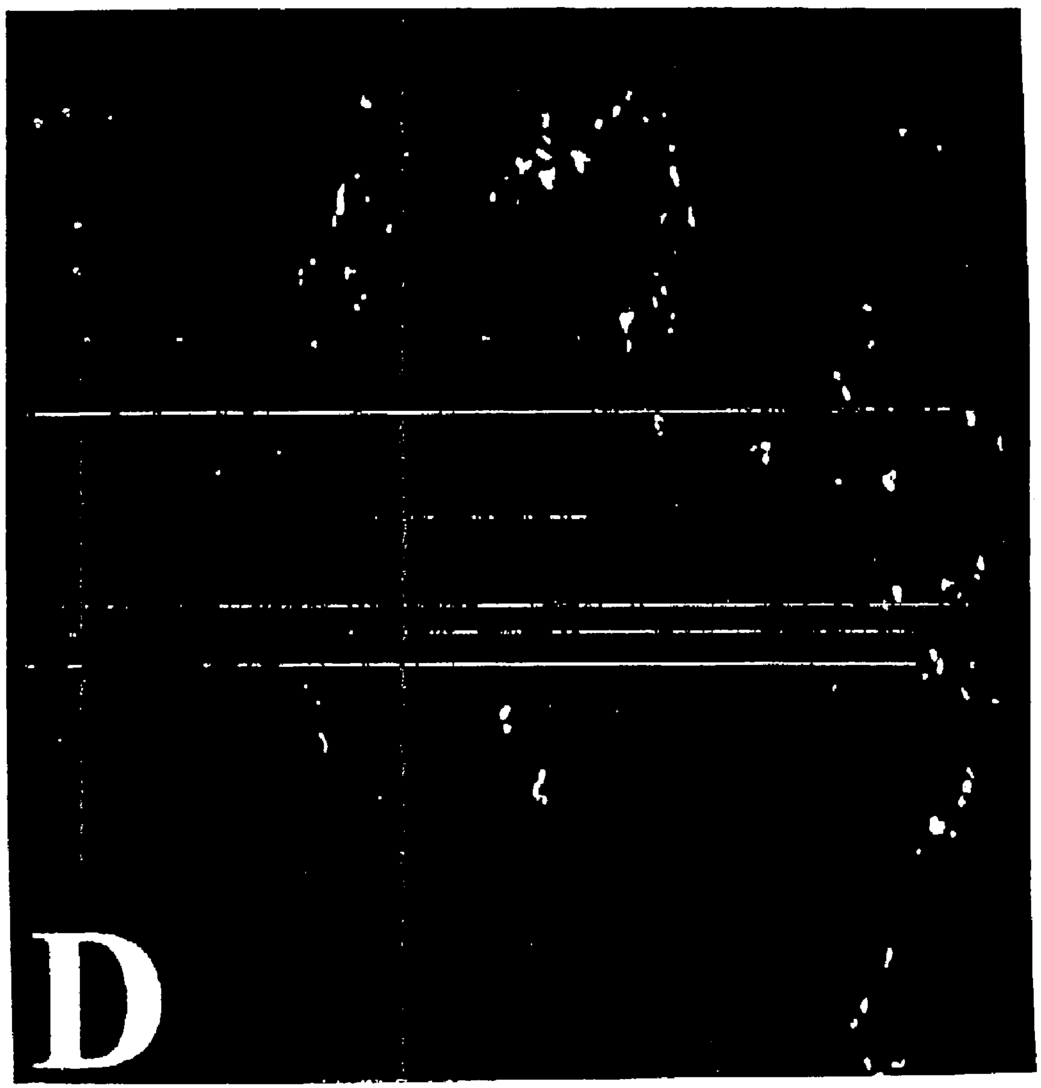
Figure 1E:
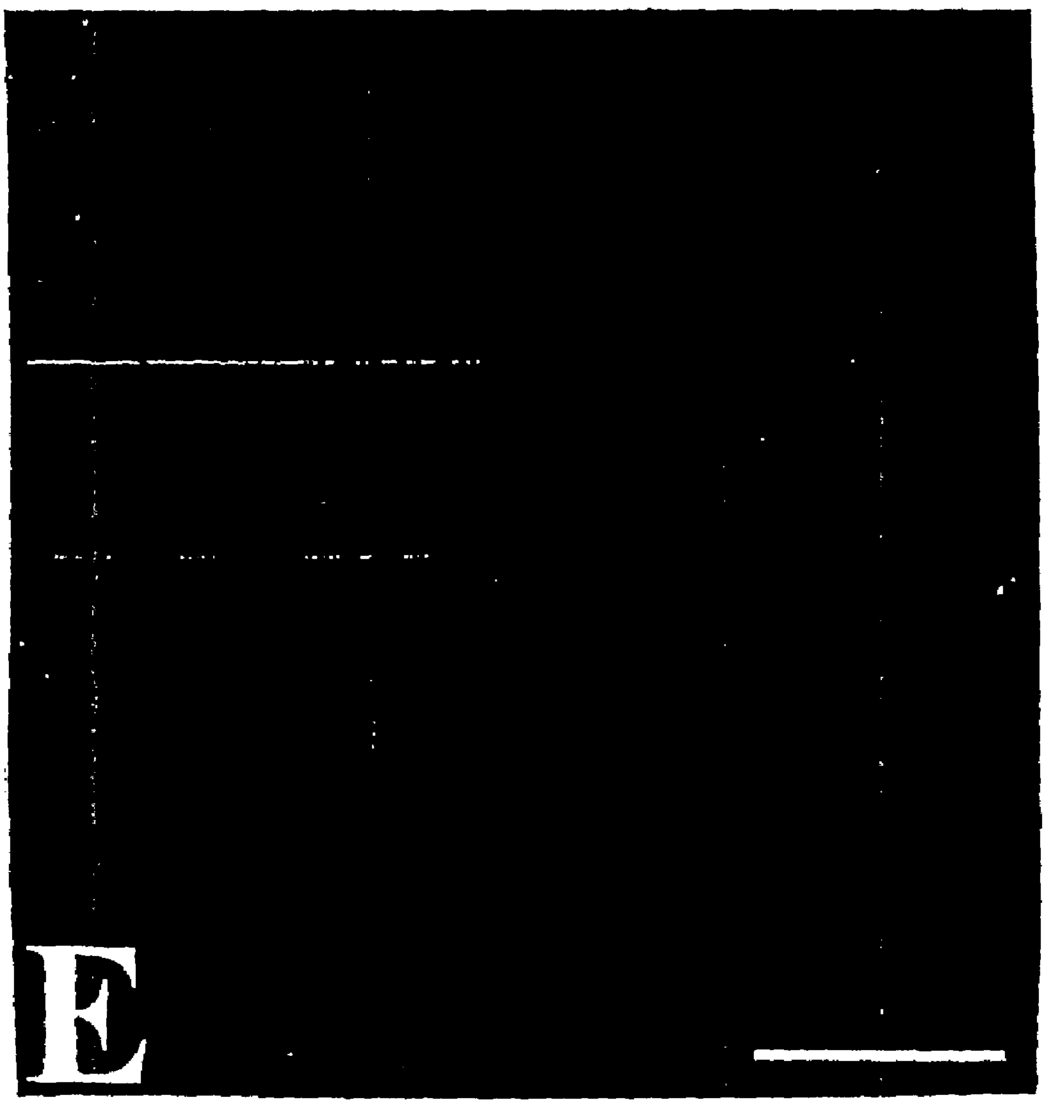
Figure 1F:
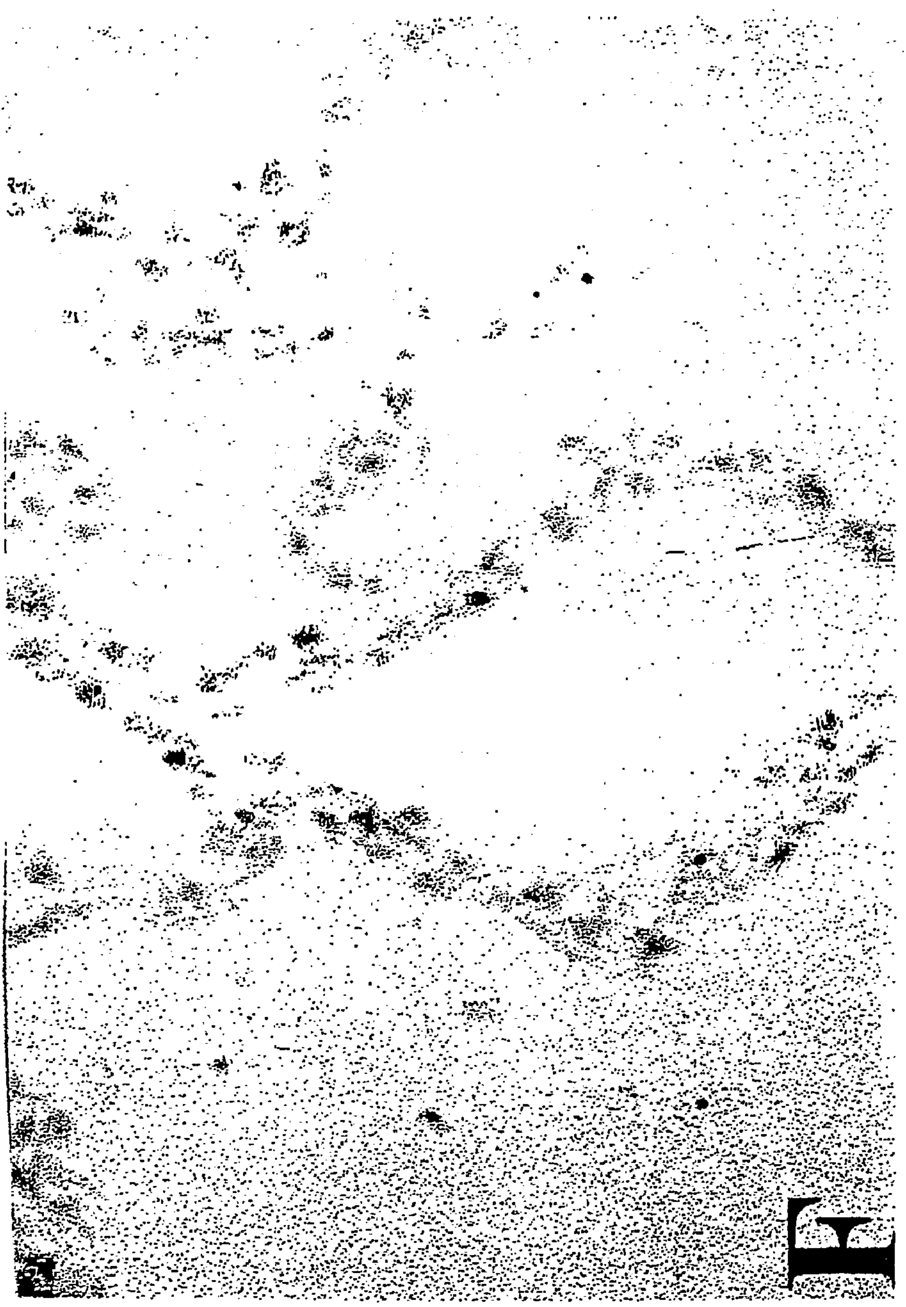
Figure 1G:
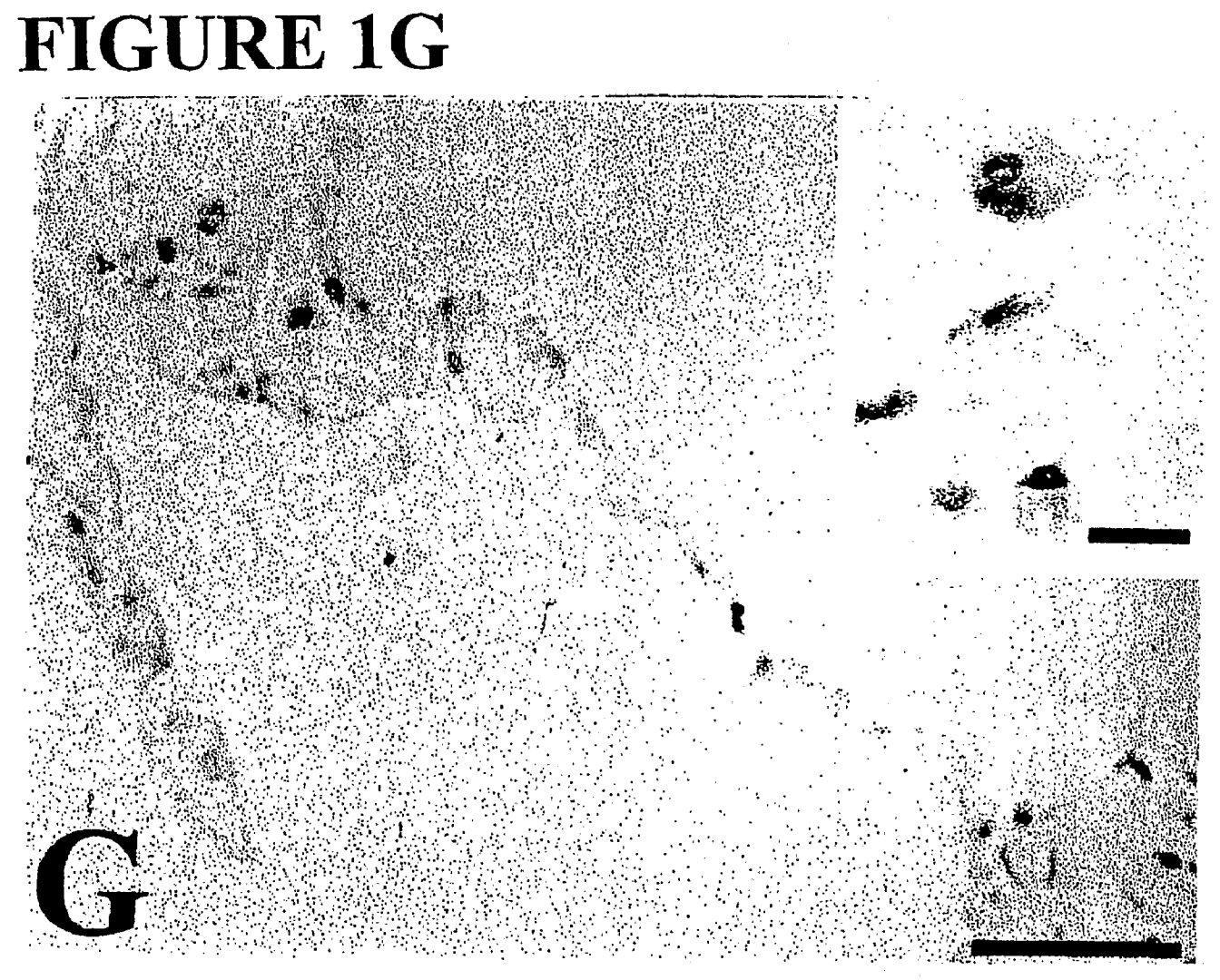

In Situ Detection of DNA Cleavage: To confirm the presence of apoptosis in the emphysema lung samples, two different TUNEL reactions were carried out. The first reaction using fluorescein-conjugated nucleotide exhibited little or no labeling in the normal lung tissue samples (FIG. 1C) while many cells with intense labeling were present throughout the emphysema tissue (FIG. 1D). Another TUNEL assay was performed using biotinylated nucleotide to identify the apoptotic cell type under the light microscope. Normal lung specimens did not react to TUNEL staining (FIG. 1F). In contrast to normal tissues, emphysema sections were TUNEL positive, however, there was no prevalent cell type. Throughout the emphysema lung specimen, alveolar and mesenchymal cells both exhibited positive TUNEL staining (FIG. 1G). In the emphysema tissue section, 6.1±3.5% (mean±1 S.D.) of cells were labeled (varied in cases from 1.3±0.3 to 12.2±3.5), whereas very few cells were positive in the normal lung samples (0.1±0.1%) ($p<0.01$). Several macrophage-like cells were TUNEL-reactive in their cytoplasm characteristic of phagocytosis of apoptotic cell bodies (FIG. 1G, inset).

Ultrastructural analysis of the emphysema lung tissue demonstrated morphological changes consistent with apoptosis in several cell types. The most prominent feature seen was cytoplasmic condensation and vacuolization, chromatin condensation and connective tissue degradation. A representative example can be seen in FIG. 2A with two apoptotic cells (arrows) in close apposition to a healthy cell; note the cytoplasmic condensation and nuclear condensation in the apoptotic cell with irregularities in the cell shape.

Figure 2B:
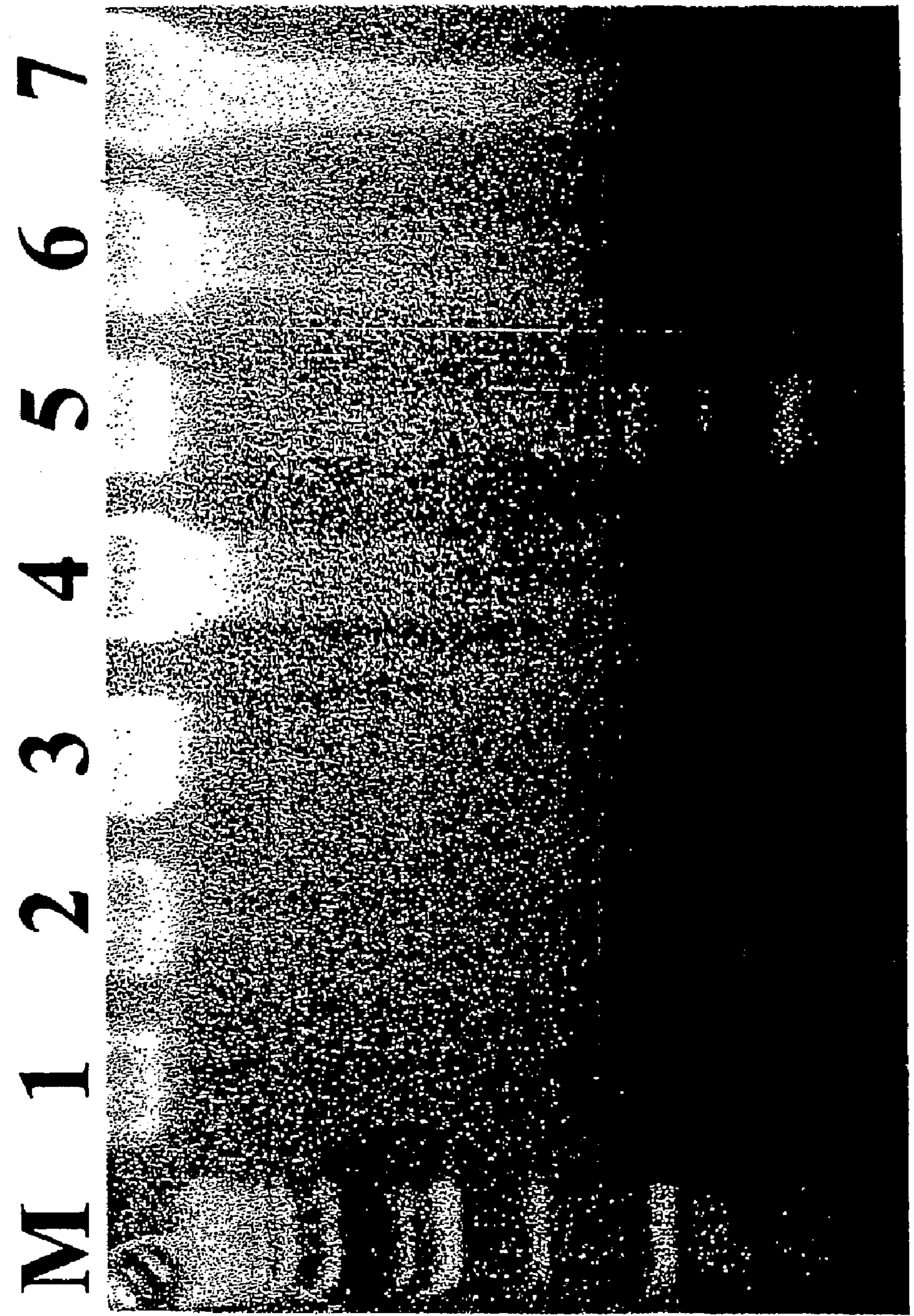

The presence of apoptosis in the emphysema lung samples was confirmed using biochemical analysis of DNA laddering (FIG. 2B). Electrophoresis of DNA isolated from emphysema tissues demonstrated degradation into small laddering fragments of multiples of approximately 180 bp subunit in contrast to the intact high Mr size seen in the normal samples.

Figures 3A, 3B:
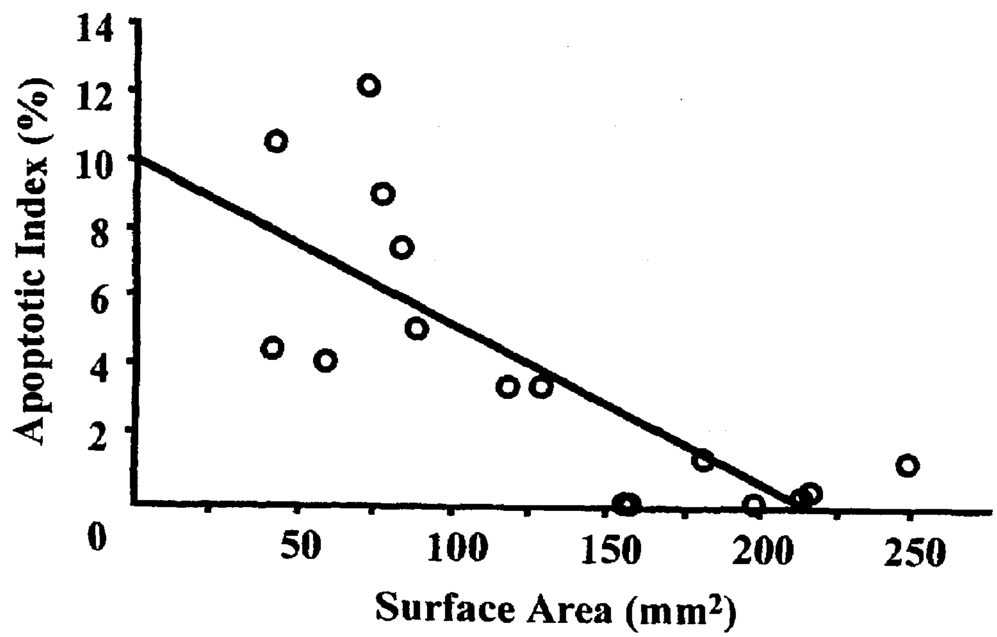

Correlation of Morphometric Measurements with Apoptotic Index Morphometric studies were performed on lung tissue examined in the above studies and surface area was calculated for each sample. Samples were divided into groups according to the severity of emphysema based on surface area measurements. There was a statistically significant association between the apoptotic index and emphysema severity ($p<0.01$) (FIG. 3A). In addition, through regression analysis the apoptotic index was shown to inversely correlate with the surface area demonstrating an increase in apoptosis with decreased surface area (FIG. 3B)

Figure 4A:
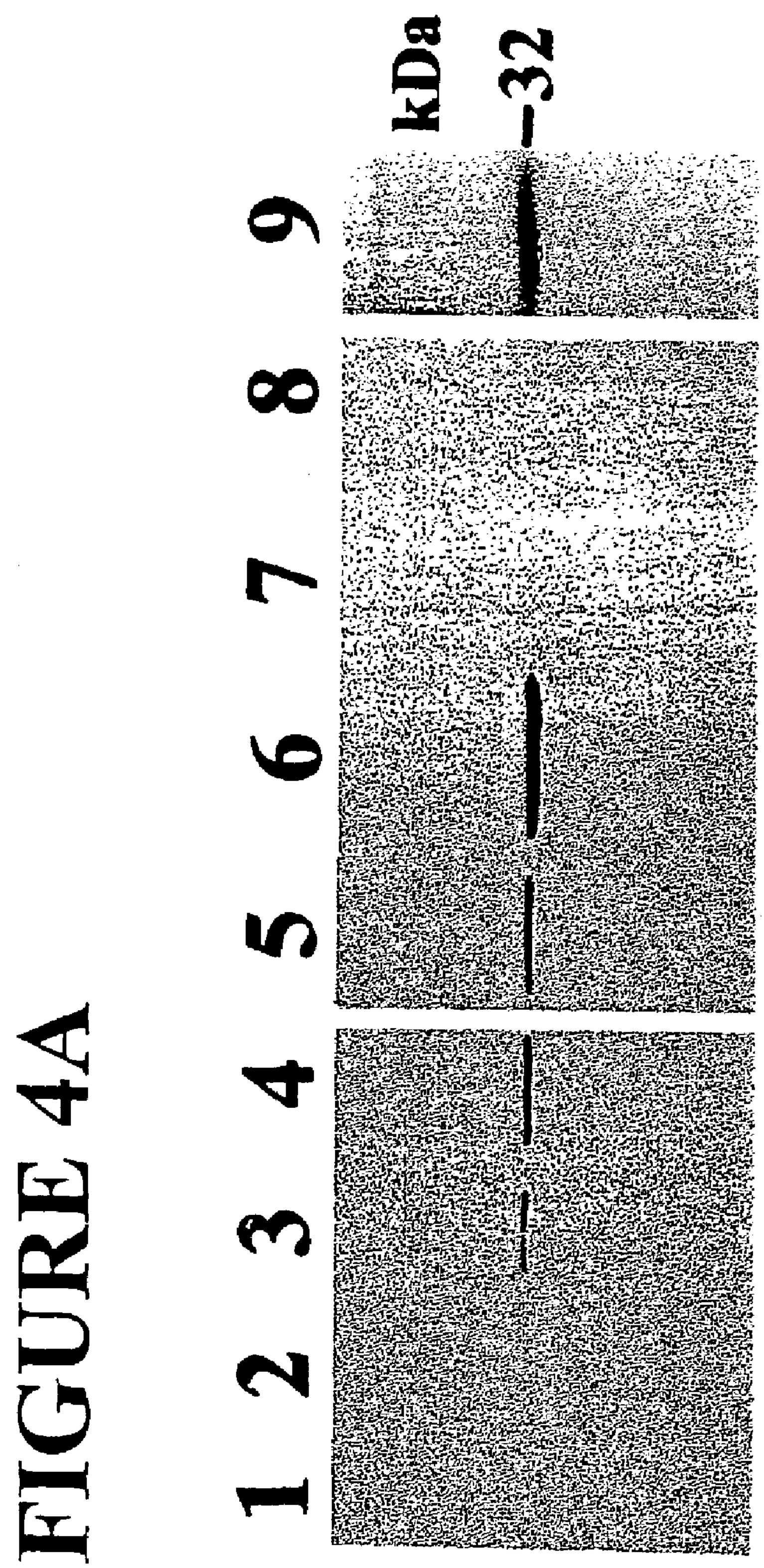
Figure 4B:
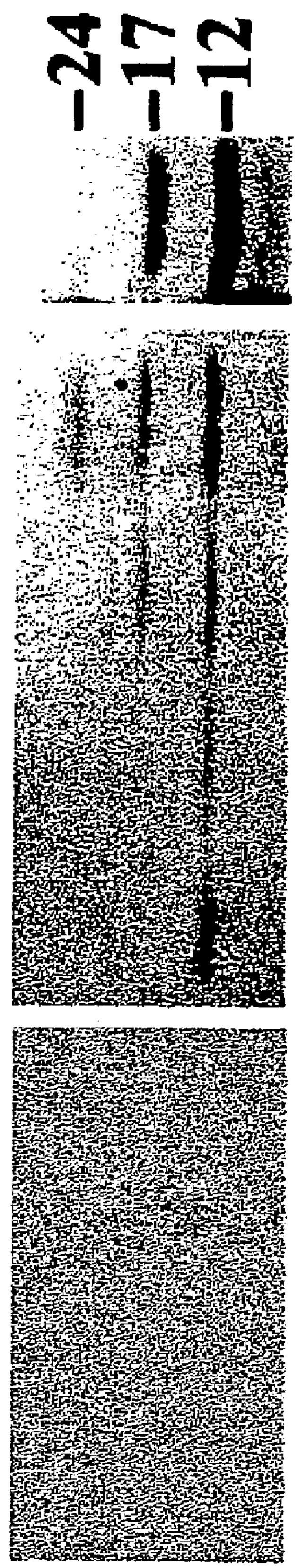
Figure 4C:
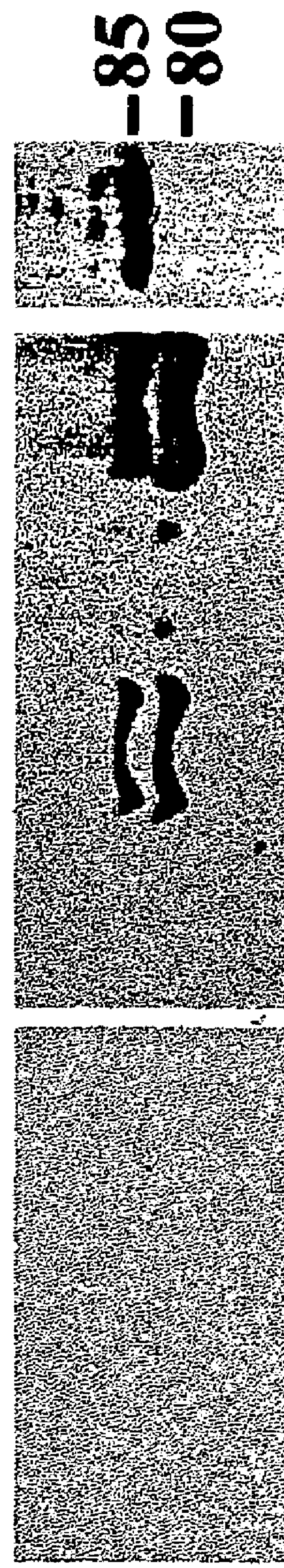

Caspase Expression, and Activity in Lung Homogenates: Aspartate-directed cysteine proteases, caspases, play a pivotal role in execution of the apoptotic pathway, but not in necrosis(15). In order to detect caspase expression, we subjected tissue homogenates directly to Western blot analysis. As shown in FIG. 4A, pro-caspase 3 (32 kDa) was detected in both normal and emphysema lung homogenates with no clear difference in expression levels in these samples. This result was confirmed by reactivity with a rabbit polyclonal antibody against caspase 3 (data not shown). The activated subunits of caspase 3 (p17 and p12) were, however, only detected in the emphysema lung homogenates (FIG. 4B). In addition, an antibody that specifically reacts to the proteolytic fragment of PARP, a substrate of caspase 3, demonstrated reactivity in the emphysema lung tissue homogenates but not in normal lung tissues (FIG. 4C). Using a fluorogenic synthetic peptide substrate caspase 3 activity was detected in the emphysema lung homogenates and not in normal lung homogenates (data not shown).

Figure 5A:
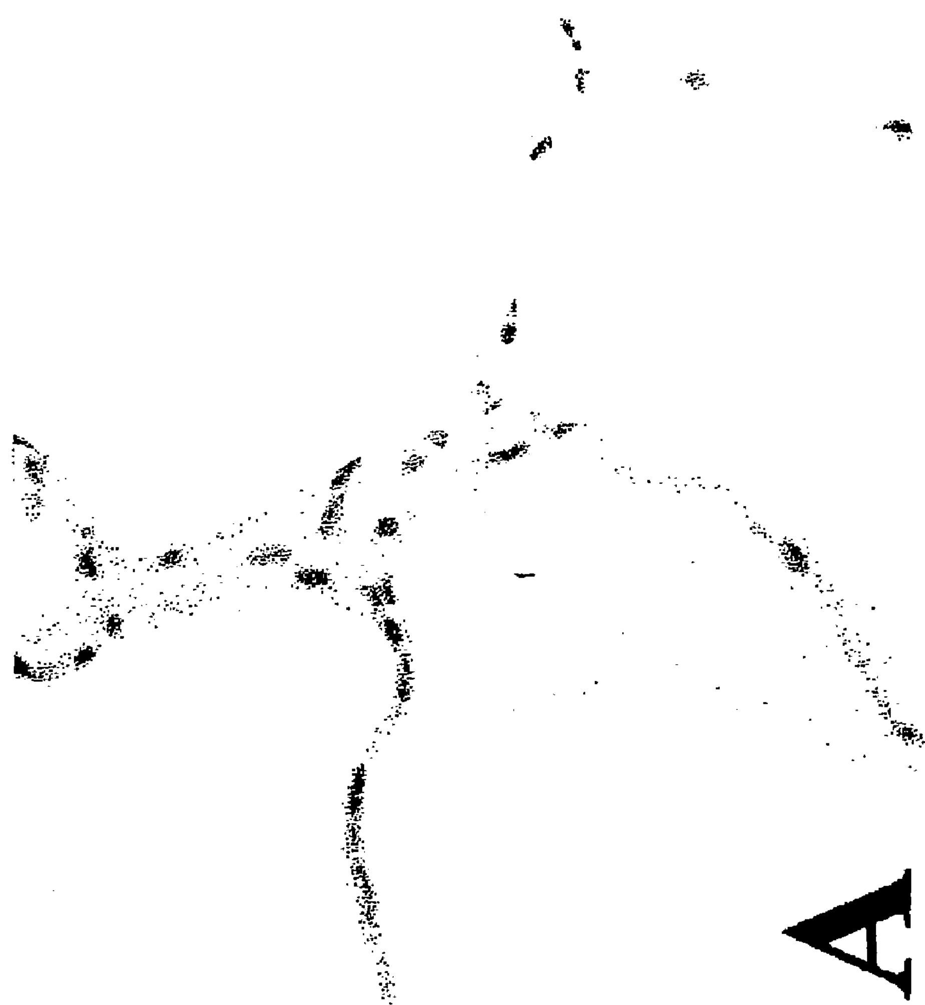
Figure 5B:
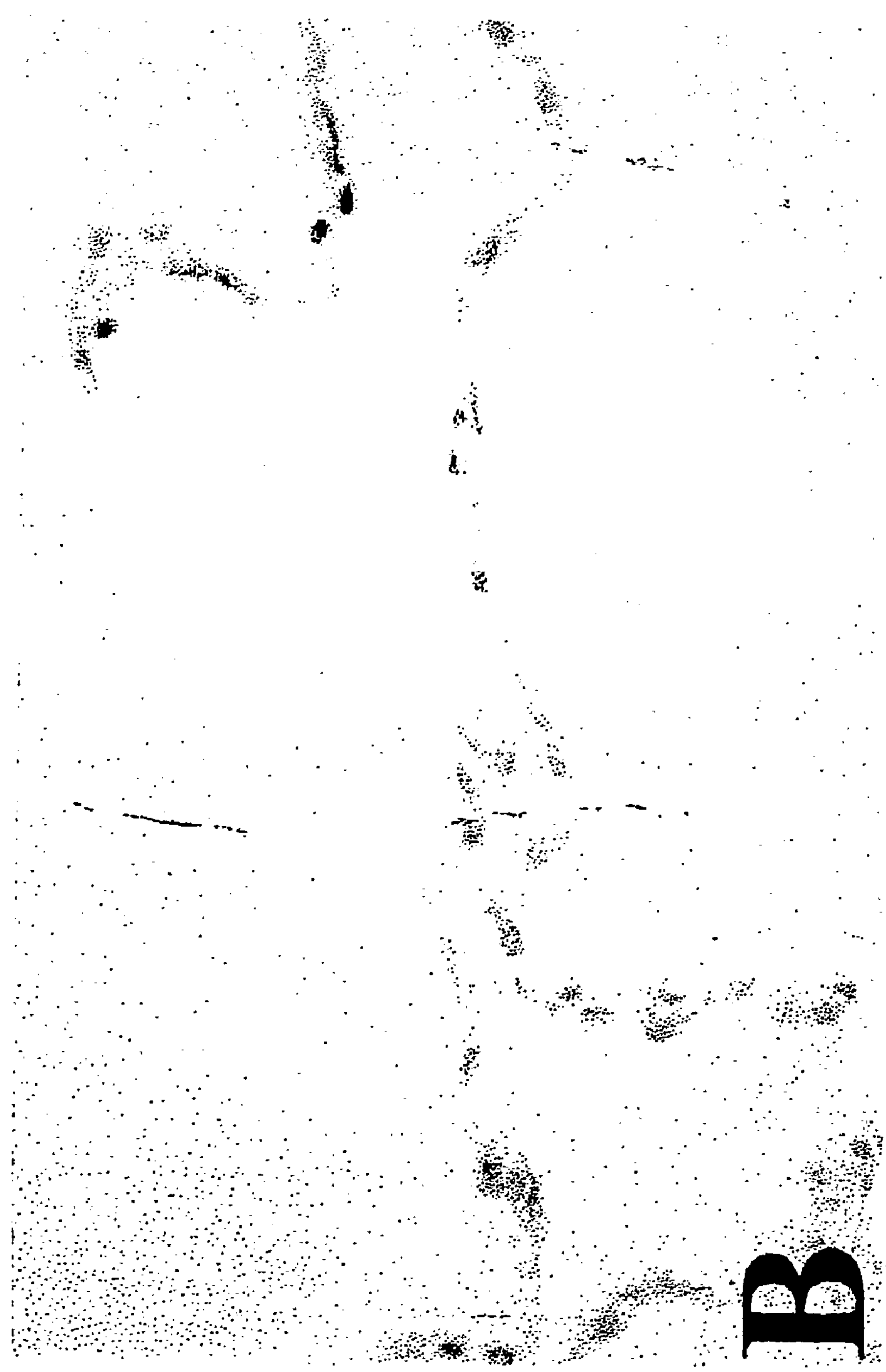
Figure 5C:
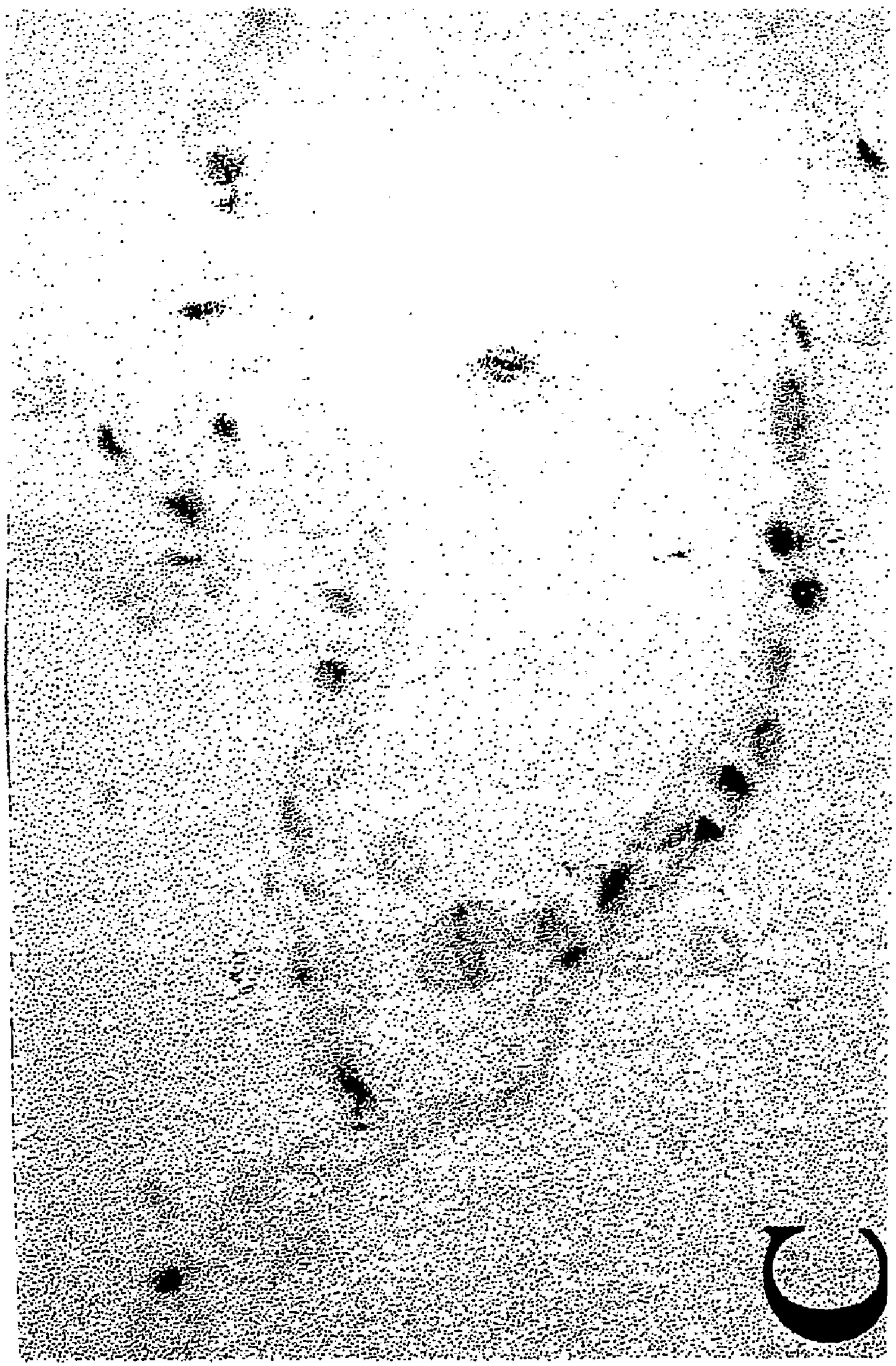
Figure 5D:
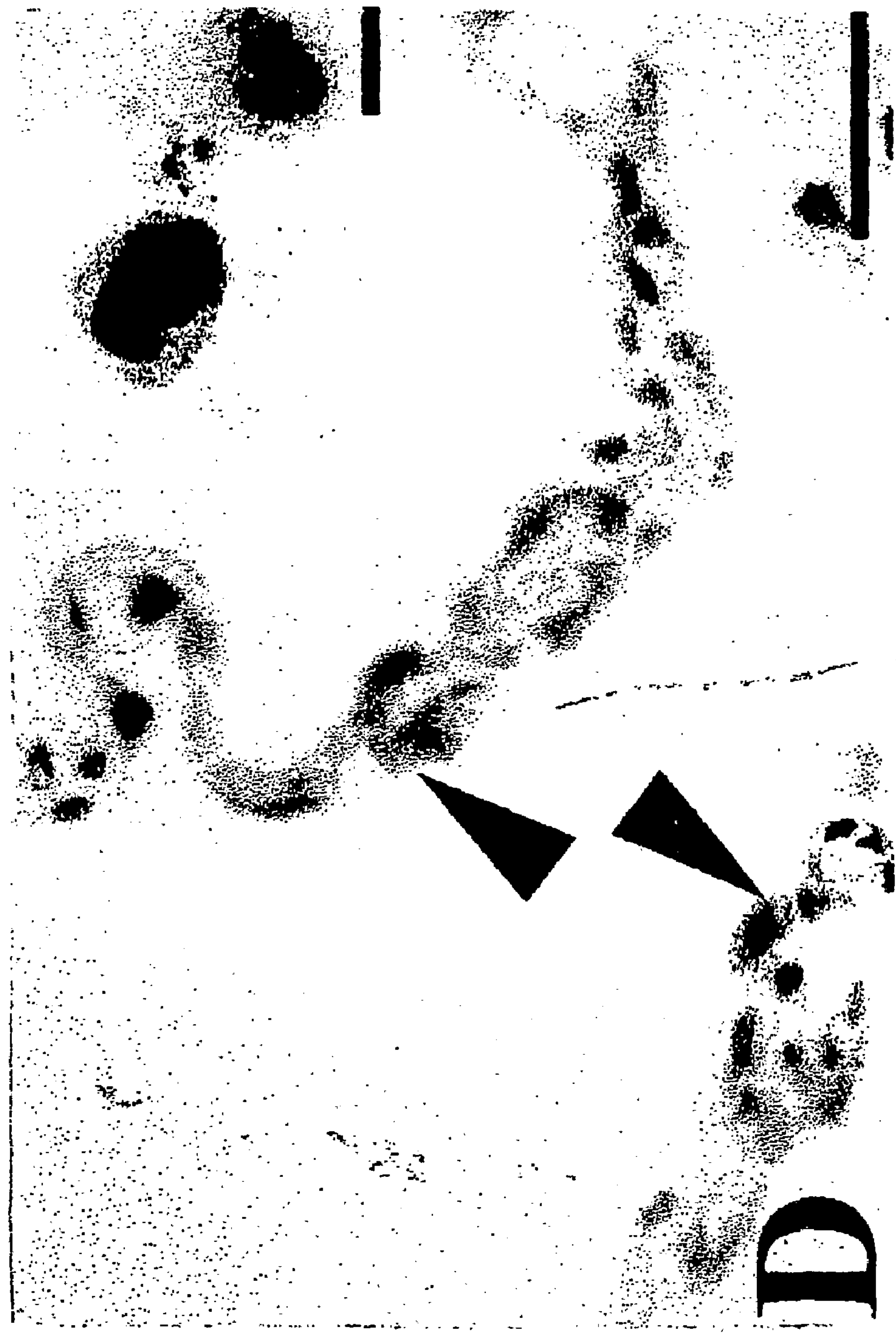
Figure 5E:
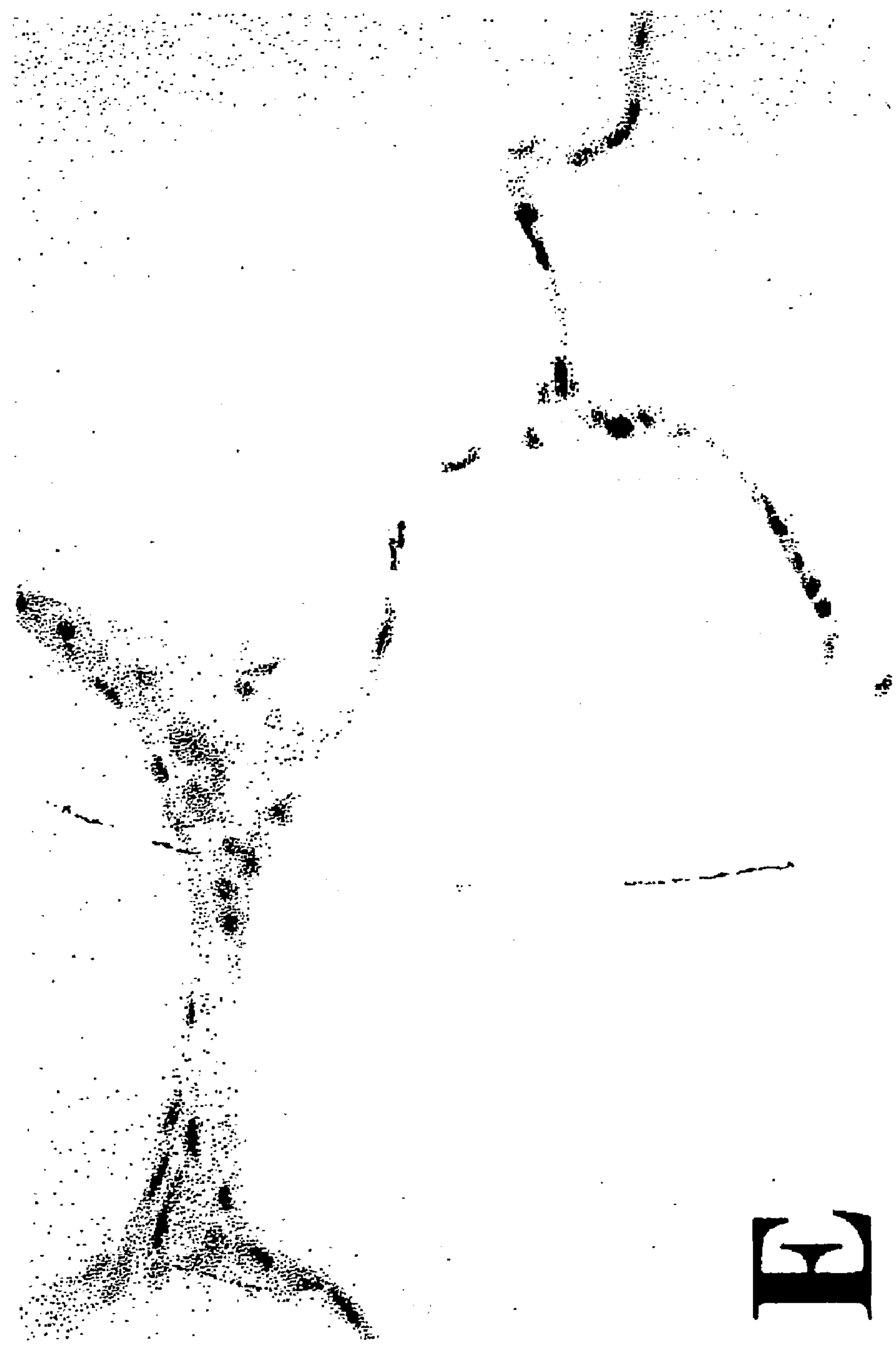
Figure 5F:
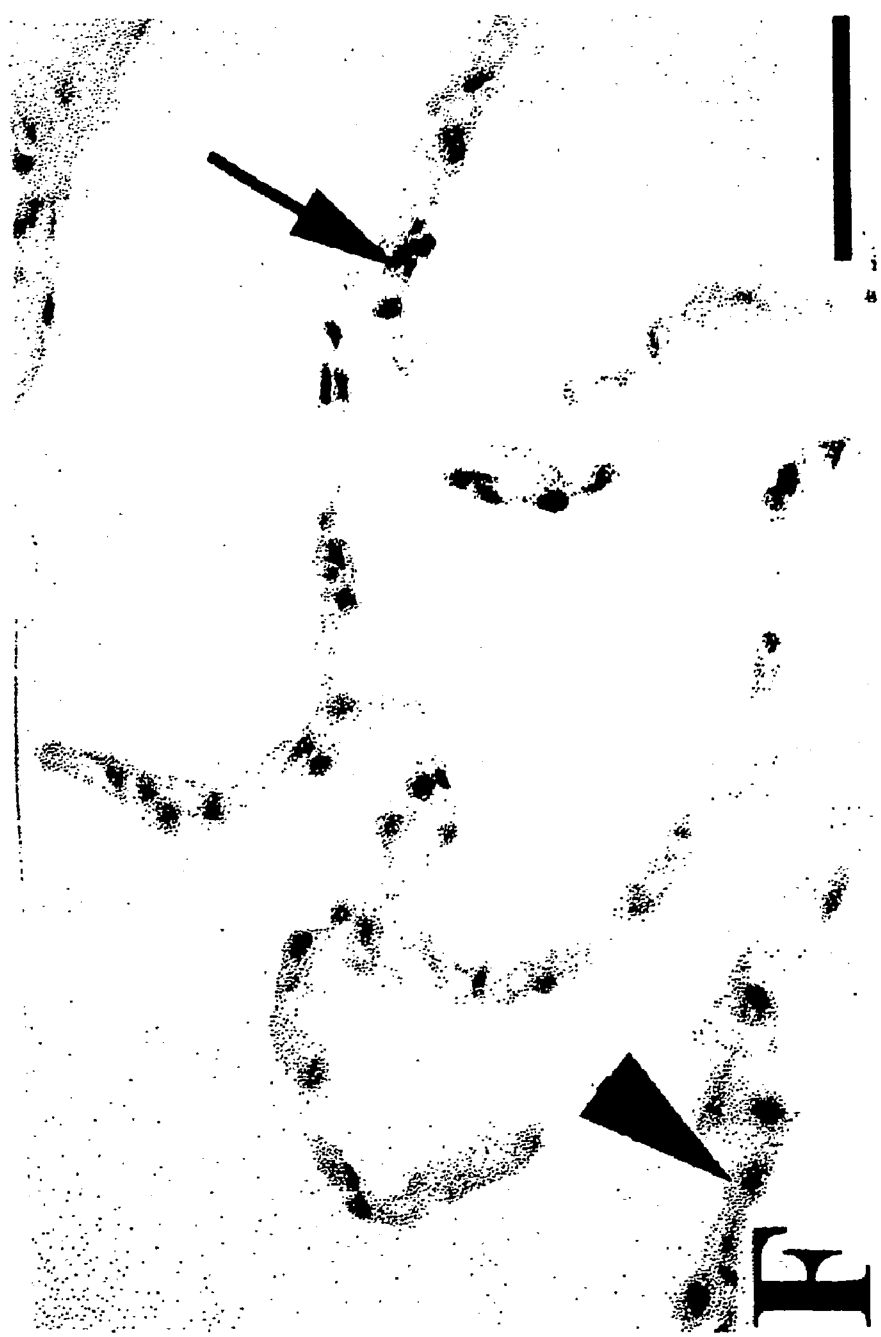

Bcl-2 and Bad Expression and Degradation of Collagen Fibrils: Recent studies indicate that the ratio of Bax protein expression to Bcl-2 expression is increased in apoptotic cells, especially when cells loose contact with extracellular matrix attachment(16, 17). Immunohistochemical analysis to detect the expression of Bcl-2, Bax and Bad was performed. Although Bcl-2 was not detected in either normal or emphysema lung tissue (FIGS. 5A and 5B), Bax and Bad reactivity was seen only in the emphysema lung samples (FIGS. 5C-F). Bax staining was localized to the epithelial cells in the emphysema lung samples (FIG. 5D, arrow, inset), whereas Bad staining was localized randomly to the epithelial and mesenchymal cells (FIG. 5F). This immunolocalization of Bad is consistent with the pattern of the TUNEL reaction. The normal lung tissue was negative for Bad immunostaining (FIG. 5E).

Discussion

In the present study, we examined morphological changes, DNA fragmentation, caspase activation and connective tissue degradation in human emphysema and normal lung tissues. Chronic obstructive pulmonary disease (COPD) is believed to be caused by exposure to cigarette smoke. However, the cellular mechanisms responsible for the progressive deterioration of respiratory function in COPD remain unclear and appear to result from architectural destruction including cellular disruption that may be associated with apoptosis. Our results demonstrate extensive cell death through apoptosis in the emphysema lungs.

Emphysema is postulated to develop from disruption of the extracellular matrix through an imbalance between proteases and antiproteases(6, 18). In the present study, we demonstrated for the first time that there is extensive cell death by apoptosis in combination with connective tissue degradation in the human emphysema lung. In this chronic disea which could be accounted for by apoptosis.

Two different mechanisms, i.e., necrosis and apoptosis are observed in cellular death. The two processes can be distinguished by distinct morphological features. Necrotic cells exhibit several characteristic features such as cellular swelling and rupture of the plasma membrane, while the nucleus remains relatively intact. Necrosis is usually associated with an inflammatory reaction which develops in the adjacent viable tissue in response to the release of cellular debris. On the other hand, cell shrinkage and blebb and intact cytoplasmic organelles morphologically characterize apoptotic cells (14). The morphological features of the emphysema lung cells in this study are consistent with apoptosis. In addition, we found evidence of DNA fragmentation in lung samples from patients with emphysema on the basis of both in situ end labeling and gel electrophoresis. The histological analysis and the TUNEL assay demonstrated no specificity in cell-types undergoing apoptosis. However, these observations are based on tissue samples at the end stage of the disease. We frequently observed TUNEL-positive material-containing macrophages in the emphysema specimens, suggesting a role for alveolar macrophages as a scavenger of apoptotic cells.

Caspase-3 processing into active species in the emphysema lung tissue, but not in the normal lung, strongly supports our observation of ongoing apoptosis in the emphysema lungs. Exclusive caspase 3 activity against a synthetic peptide in the emphysema samples confirms this observation. The sequence of caspase activation is an indispensable process in the apoptosis pathway(19). Caspase 3 functions down-stream of cell damage in the apoptotic pathway and has a pivotal role in targeting molecules for proteolysis. Proteolysis of PARP by caspase 3 is a specific event that occurs during apoptosis(19). Detectable degradation of PARP into an 85 kDa fragment was observed in the emphysema tissue samples indicating caspase activity in the emphysema tissues but not in the normal lungs.

The close correlation of apoptosis with the morphological parameters of the disease was demonstrated in this study. Although the apoptotic index was variable between patient samples, statistical analysis demonstrates that the increase in apoptotic cell death associates with more severe structural destruction of the lung. When comparing the apoptotic index with morphometric measurements of emphysema this study strongly demonstrates a correlation between apoptosis and severity of disease and emphasizes the potential involvement of apoptosis in emphysema progression. The direct mechanism of apoptosis in human studies is not easily identifiable, however, intuitively the disruption of the extracellular matrix through the known protease-antiprotease imbalance could lead to induction of the cellular death program. The presence of apoptosis in the lung does not negate the role of proteases in the pathogenesis of the disease and may be a continuum in the process of destruction. The failure of the lung to maintain its cellular architecture in the presence of excess proteases may ultimately lead to the induction of apoptosis. It is known that expression of pro-apoptotic Bax family members is increased when cells are dying through depletion of cell adhesion to the extracellular matrix(16, 17) The Bax family members counteract Bcl-2 function and trigger caspase activation. Our immunostaining data suggests that there is an increase of Bax protein staining in contrast to Bcl-2 in the emphysema tissue. It is known that in emphysema tissue there is extensive loss of the extracellular matrix leading to massive connective tissue damage in the emphysema alveolus(20). Furthermore, TUNNEL positive staining was seen in a transgenic mouse model of emphysema (7) as compared to the wild-type litter mates (Imai et al, unpublished results). This transgenic model develops emphysema as a result of collagenase disruption of the extracellular matrix.(7) Immunoreactivity to anti-Bad antibody was also increased in the emphysema lungs. Although a role for increased Bad expression has not been defined, Bad is known to counteract Bcl-2 induced apoptosis. Therefore, the combination of increased Bax and Bad staining, increased apoptosis in the transgenic mouse and loss of the extracellular matrix in emphysema leads us to hypothesize that connective tissue degradation in the alveolar septa abrogates the cell-matrix attachment and contributes to induction of apoptosis.

Recently, we identified emphysema specific expression of secreted frizzled-related protein using a differential display assay(21). This molecule inhibits Wnt binding to its cell surface receptor frizzled. Although targeting of the Wnt signal in mammals is not well defined, expression of the exogenous Wnt gene in cultured cells promotes cellular proliferation(22). Interestingly, secreted frizzled-related protein was also identified as an apoptosis-inducing protein in cultivated cells(23, 24). Thus, the inhibition of the Wnt signaling pathway could possibly be involved in the apoptosis seen in the emphysema lung.

In the present study, we demonstrate for the first time that extensive apoptosis is occurring in emphysema lung. This is an intriguing novel mechanism in which to explain the destruction of the lung during progression of the disease. This is the first demonstration in emphysema that cellular loss in addition to matrix loss plays a role in the disease process. Recent studies demonstrated that apoptosis is occurring in a variety of chronic human diseases including neurodegenerative disease, heart failure, atherosclerosis, and viral diseases(19, 25). In several of these diseases, anti-apoptotic agents are expected to treat patients or slow disease progression and many of those agents are under evaluation and could potentially be applied to emphysema.

Conclusions

Lungs from all emphysema samples, but not normal controls, showed evidence of DNA fragmentation as determined by TUNNEL assays. In agreement with the positive TUNNEL assays, the emphysema lung samples also exhibited DNA indicative of cells undergoing apoptosis. Western blot analysis exhibited expression of activated caspase 3 and the presence of a specific cleavage product of poly(ADP-ribose) polymerase. Finally, immunohistochemistry demonstrated increased expression of pro-apoptotic molecules Bax and Bad in the emphysema lung samples with no increase in BCL-2.

The novel demonstration of apoptosis in the emphysema lung suggests that programmed cell death contributes to the progressive loss of respiratory function in this disease. Therefore, disrupting the apoptotic pathway could be an alternative approach to therapy in humans.

Example 2

Activation of an Embryonically Expressed Gene in Pulmonary Emphysema. Identification of the Secreted Frizzled-related Protein.

Differential display analysis was performed on lung tissue to identify genes expressed in emphysema but not in normal lung. Secreted frizzled-related protein 1 (sFRP1), an inhibitor of wnt signaling, was found to be expressed in emphysema but not in normal lung tissue. Other members of the sFRP family did not demonstrate differential expression in lung tissue. Expression of the mouse homologue, sFrp1, was also detectable only in emphysema and not in normal lungs of mice. Finally, embryonic-specific expression of sFrp1 suggests that the Wnt signaling pathway is normally involved in lung development. The novel identification of an embryonic gene activated in emphysema provides insight into the pathophysiological changes in this disease.

Figures 6A, 6B, 6C:
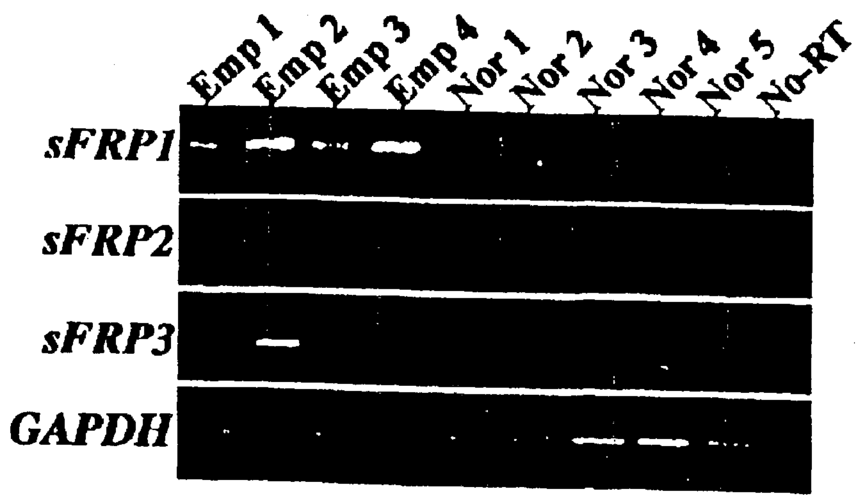

In this Example, RNA fingerprinting (27) was used to compare expressed genes between emphysema and normal human lung tissue (FIG. 6A). After subcloning 30 gene candidates that were differentially expressed, a dot blot hybridization was performed using the first strand cDNA from normal and human emphysema lung samples as probes for secondary screening. Nine of these clones led to one-sided signals between the two probes (FIG. 6B). Five clones were expressed only in the emphysema lung sample and four clones were expressed only in the normal lung sample. These clones were subjected to DNA sequence analyses. Based on sequence data, reverse transcription (RT)-PCR was performed to verify the expression pattern of these genes. Through RT-PCR, clone 1-41 was shown to be expressed in the emphysema lung samples but not detected in the normal lung (FIG. 6C). None of the other clones demonstrated such an absolute difference in their pattern of "expression (data not shown) and thus these clones were not analyzed further.

A search of the Genbank database revealed partial homology of clone 1-41 to mouse and bovine secreted frizzled-related protein 1 (sFrp1).(28, 29) In addition, a search of the expressed sequence tag (EST) database localized this sequence to the chromosomal region of 8p11-12 (A002C42, stSG3941), between D8S1791-D8S268 (NCBI accession no.: W21306, H29416, H29323, H16861, H16753 and H12000). This chromosomal site is identical to the chromosomal site of the human sFRP1 gene.(26) 5'RACE was performed to identify the upstream sequence of clone 1-41 and a 1.1 kb cDNA fragment was obtained. The upstream 530 bp of the 5'-end sequence of clone 1-41 demonstrated 97% identity to the 3'-end of the human sFRP1 gene.(26) Therefore, we considered clone 1-41 to be the 3'-end of the human sFRP1 gene and used the open reading frame sequence from human sFRP1 in subsequent experiments.

sFRP1 belongs to a gene family of five molecules, sFRP1~sFRPS.(29-32, 26) Through RT-PCR analysis the expression pattern of the sFRP family members were examined. Only sFRP1 was found to be expressed in emphysema and not in the normal lung tissue. sFRP2 and sFRPS were not detected in any of the samples (FIG. 6C). sFRP3 was detected in only one of four emphysema lungs and in none of the normal lung samples (FIG. 6C). sFRP4 was detected in all of the emphysema and normal lung samples as demonstrated in previous studies (data not shown).(26, 30, 31, 33)

Animal models of emphysema have been developed which help in understanding the pathogenesis of emphysema.(34-35) Transgenic mice which express human interstitial collagenase in the lung develop emphysema strikingly similar to the human disease.(7) The smoke-exposed mouse has also been used as a mouse model of emphysema.(35) Although expression of the mouse sFrp1 homologue was not observed in the normal adult mouse lung, both transgenic and smoke-exposed mice expressed sFrp1 (FIG. 7). The mouse homologue for sFrp3 was not amplified in any samples examined (data not shown).(28)

To rule out the possibility that sFrp1 was induced solely through nonspecific injury to the lung, intraperitoneal injections of lipopolysaccharide (LPS) were given to mice.

Systemic administration of LPS results in increasing proinflammatory cytokines in the lung and induction of acute phase inflammatory proteins such as haptoglobin.(36) LPS injection in the mice did not upregulate sFrp1 expression in the lung, but, as expected, haptoglobin expression was induced (data not shown). This result indicates that induction of sFrp1 is related specifically to the pathological changes which occur in emphysema.

Expression of sFrp1 in the embryonic developmental lung was examined. Although re-expression of developmentally regulated genes has been found in a variety of diseases(37), this has never been observed or noted in emphysema. Specific amplification of the sFrp1 PCR product was observed in the embryonic mouse lungs (14 and 18 dpc) in contrast to no detectable expression in the newborn and adult lungs (FIG. 7).

The biological activity of sFRPs is closely related to the function of the Wnt family of proteins. The basic structure of sFRP is homologous to the extracellular Wnt-binding domain of Frizzled (FZ), the Wnt cell surface receptor(32), but lacks the seven transmembrane spanning sequence that anchors the protein to the cell surface and transmits Wnt signaling-activities(32). Therefore, sFRPs are believed to inhibit the Wnt-inducible signaling pathway by antagonizing Wnt-FZ binding in the extracellular milieu(32). The interaction of each specific sFRP with its respective Wnt molecule has not been defined. Therefore we wished to examine if any Wnt molecules were. expressed in the lung. The Wnt family is divided into two classes according to their ability to transform mammary epithelial cells and cause axis-induction in *Xenopus* (Wntl class and WntSA class). (32) In this study, WNT1 and 8B (Wntl class) mRNA was not amplified in human lungs. However, the WNT5A transcript was detected in all of the emphysema samples and two of the five normal samples (FIG. 8). These studies on Wnt lead to the conclusion that the WntSA class is expressed in the lung and suggest that this class of proteins may be a potential target of sFRP1 inhibition in emphysema.

Four members of the human FZ family have been isolated, HZD2, HZD3, HFZ5 and HFZ6.(31) Expression of these genes in the lung has not yet been defined. Through RT-PCR analysis, HZD2 was found to be expressed in three of the four emphysema and four of the five normal lungs (FIG. 8). HFZ6 was present in all of the samples (FIG. 8). HZD3 and HFZ5 were not amplified by the PCR reactions (data not shown). The demonstration of WNT and FZ (HZD2 and HFZ6) within the lung confirms that the signaling machinery for the sFRP is indeed present within the lung.

Expression of sFRP1 was observed exclusively during embryogenesis in the lung. The identification of sFRP1 in the embryonic lung will lead to future studies which identify the cell type of expression and the interactions with specific FZ and Wnt family genes in lung development. Intriguingly, sFRP1 is expressed in the adult tissue when the lung is injured in emphysema. The specific elevated expression of sFRP1 in emphysema was not a generalized phenomenon for all members of this gene family, because the expression sFRP2-sFRP5 was not altered between emphysema and normal lung samples. The presence of sFRP1 in emphysema demonstrates for the first time developmental gene re-expression in this disease. The Wnt signaling pathway plays a pivotal role during embryogenesis and in the state of tissue injury in emphysema this process could be recapitulated. The re-expression of developmentally regulated genes in this disease may reflect a protective role for sFRP1 during the repair process. Emphysema is characterized by extensive chronic destruction of the lung architecture and is associated with a variety of tissue reactions. Investigators have focused primarily on the role of proteases and anti-proteases in this disease process.(4) However, this study demonstrates a novel molecular pathway involving Wnt signaling in the pathophysiology of emphysema. Further avenues of research will define the link between sFRP1 expression and the specific Wnt signaling pathway and elucidate the role of this pathway in lung disease.

Methods.

Lung Samples. Six cases of human emphysema lung tissue were obtained at Columbia Presbyterian Medical Center from recipient lungs during transplantation or lung volume reduction procedures. The major etiological factor for emphysema in these patients was cigarette smoking. All samples were taken from patients who reportedly stopped smoking for at least three months (mean age±S.D., 47±11 years). Five normal lungs were obtained from donor lungs harvested for transplant but not used due to recipient complications. All of the normal samples were obtained from non-smokers.

The smoke-exposed mouse is generally used as an animal model to develop emphysema after 6 months of exposure to cigarette smoke.(35) Six-month-old mice were •subjected to smoke from two non-filtered cigarettes per day. After 6 months, the mice were sacrificed for lung excision. A transgenic mouse model was used which overexpresses human interstitial collagenase in the lung develops emphysema.(7) The lungs were removed from five-month-old mice. For developmental analysis, the lungs of 14 and 18 dpc embryos and newborn wild-type mice were collected. For induction of the acute phase reaction with LPS (Sigma, St. Louis, Mo.), mice were given intraperitoneal injections of saline or LPS. Animals were killed 24 h after intraperitoneal injections.(36) Total RNA was isolated from lung, heart, kidney and liver tissues as described above.

Differential Display. Total RNA was prepared from fresh tissue by the guanidinium thiocyanate-cecium chloride method. Differential display was performed using RNAimage (GeneHunter Corp., Nashville, Tenn.). Total RNA (0.2 mg) was reverse transcribed with three different one-base-anchored oligo(dT) primers (H-T, ,M, M=G, C or A). The reactions were performed for each RNA sample in 25 mM Tris-HCl, pH 8.3, 37.6 mM KCl, 1.5 mM $MgCl_2$, 5 mM DTT, 20 uM of each dNTP, and 0.2 uM of H-$T_{11}$M. The solutions were heated to 65° C. for 10 min and cooled at 37° C. for 10 min, after which 100 U of MMLV reverse transcriptase were added. After incubation at 37° C. for 50 min, the mixture was heated to 75° C. for 5 min to inactivate the transcriptase before storage at −20° C. The PCR mixture contained 0.1 volume of the RT reaction, 20 mM Tris-HCl, pH 8.4, 50 mM KCl, 2.0 mM MgCl, 2 uM of each dGTP, dTTP and dGTP, a-[$^{33}$P]dATP (2,000 Ci/mmole, NEN, Boston, Mass.), 0.2 mM of arbitrary 13-mer primer, 0.2 mM of the respective H-$T_U$M oligonucleotide and Taq DNA polymerase (Gibco BRL, Gaithursberg, Md.). Each PCR amplification was carried out for 40 cycles at 94° C. for 30 sec, at 40° C. for 2 min, and at 72° C. for 30 sec, followed by 5 min postextension at 72° C. Radiolabeled PCR amplification products were analyzed by electrophoresis on denaturing 6% polyacrylamide gels, and the dried gels were exposed to X-ray film. Four independent samples from two emphysema lungs and two normal lungs were compared side by side on gels to confirm the reproducibility of banding patterns.

Subcloning and Verification of Bands. Bands of interest ranging from 150 to 800 bp were recovered from the gels and reamplified in a 40 cycle PCR reaction in the absence of isotope. The reamplified PCR bands were subcloned into a pGEM-T Easy Vector (Promega, Madison, Wis.). Individual clones (1 lig) were spotted on a nitrocellulose membrane (Protran, Schleicher & Schuell, Keene, N.H.) in a 96-well format (Schleicher & Schuell). The membranes were then hybridized with $^{32}$P-labeled first strand cDNA prepared by RT of total RNA of normal or emphysema lungs using an oligo $(dT)_{12-18}$ primer (Gibco BRL). Hybridized clones to either the emphysema or normal lung probe were used for sequence analysis. The sequences were queried against the National Center for Biotechnology Information (NCBI) database using the Basic Local Alignment Search Tool (BLAST) algorism. To verify expression patterns of genes in vivo, DNA-free total RNA was prepared and converted to a first-stranded cDNA using a random primer (Gibco BRL) and Superscript II (Gibco BRL) followed by PCR amplification. The primer sets (20-mer) to each gene were designed and used for verification of specific expression in either the normal or emphysema sample.

5'RACE. 5'RACE was performed basically according to the manufacturer's instruction (5'RACE System for Rapid Amplification of cDNA Ends, Gibco BRL). Poly(A) RNA was reverse transcribed with oligo$(dT)_{12-18}$ primer and Superscript II followed by RNA digestion of the first strand cDNA. A homopolymeric tail was added to the 3'-end of the cDNA using terminal deoxynucleotidyl transferase and dCTP, which allows hybridization to the Abridged Anchor Primer in subsequent PCR reactions. PCR reactions were performed with primer sets of the Abridged Anchor Primer and the gene specific primer, and Taq/Pwo DNA polymerase Mix (Boehringer Mannheim, Indianapolis, Ind.). The second PCR reaction was carried out using the first PCR reactions as templates, the Abridged Universal Amplification Primer and a 3'-nested gene specific primer. Amplified fragments were subcloned into pGEM-T Easy Vector and sequenced.

RT-PCR Specific primer sets used are shown below.

```
sFRP1;      Forward 5'-TACAAGAAGATGGTGCTGCC-3',
            Reverse 5'-AGCACAAGCTTCTTCAGGTC-3',
Nested      Reverse 5'-AGATGTTCAATGATGGCCTC-3':
sFRP2;      Forward 5'-TCTTCCTCTTTGGCCAGCCC-3',
            Reverse 5'-TCACATCAATTTGGAGCTTC-3':
sFRP3;      Forward 5'-TCTGCACCATTGACTTCCAG-3',
            Reverse 5'-TCTCAGCTATAGAGCCTTCC-3',
Nested      Reverse 5'-TTAGAATCTCCTTCACCTCC-3':
sFRP4-      Forward 5'-TCCTGGCCATCGAGCAGTAC-3',
            Reverse 5'-GATGAGGACTTGAAGATCTC-3':
s F R P 5;  Forward 5'-ACTCGGATACGCAGGTCTTC-3',
            Reverse 5'-TTCTTGTCCCAGCGGTAGAC-3':
WNT1;       Forward 5'-TCCTCCACGAACCTGCTTAC-3',
            Reverse 5'-ACATCCCGTGGCACTTGCAC-3',
Nested      Reverse 5'-TTCGATGGAACCTTCTGAGC-3':
WNT5A;      Forward 5'-GACAGAAGAAACTGTGCCAC-3',
            Reverse 5'-TGTCTTCAGGCTACATGAGC-3':
W N T 8 B;  Forward 5'-CGCAAGTATCAGTTTGCCTG-3',
            Reverse 5'-TAGAGATGGAGCGAAAGGTG-3',
Nested      Reverse 5'-TGGTACTTCTCCTTCAGGTG-3':
```

-continued

```
HZD2;         Forward 5'-TCTCAGCTACAAGTTTCTGG-3',

              Reverse 5'-CCATGCTGAAGAAGTAGAGC-3':

HZD3;         Forward 5'-TGTGCTACAACGTCTACTCG-3',

              Reverse 5'-ATGAGCTTCTCCAGCTTCTC-3':

HFZ5;         Forward 5'-TCCTATGCACTATGTACACG-3',

              Reverse 5'-TGTCCATGTCGATGAGGAAG-3':

HFZ6;         Forward 5'-TGGATTTTGGTGTCCAAGGC-3',

              Reverse 5'-AAGAATCACCCACCACACAG-3':

GAPDH;        Forward 5'-TTCCACCCATGGCAAATTCC-3',

              Reverse 5'-TTTCTAGACGGCAGGTCAGG-3':

sFrp1;        Forward 5'-AGCGACGTGCAAAAGGAGAG-3',

              Reverse 5'-AGCCTGAAATGCCTCATGTC-3':

sFrp3\        Forward 5'-ACATGACCAAGATGCCCAAC-3',

              Reverse 5'-TCCCTTGGAATGTTTACCAG-3':

G a p d h;    Forward 5'-ATGCATCCTGTACCACCAAC-3',

              Reverse 5'-TGGTCCTCTGTGTAAGCAAG-3'.
```

After the RT reaction of total RNA using Superscript II, the same PCR reaction described above was performed with an annealing temperature of 52° C. for sFRP1 and 3, 58° C. for sFRP2, 4 and 5, WNT1, 5A and 8B, HZD2 and 3, HFZ5 and 6, and sFrp1 and 3, 50° C. for GAPDH and Gapdh. Nested PCR was carried out for sFRP1 and 3, and WNT1 and SB.(38) Amplicons were then analyzed on a 2% agarose gel.

Example 3

Transfection of sFRP-1 Gene Induces Apoptosis Without Preference to Cell-type Examined We have shown that sFRP-1 is upregulated in emphysema through differential display.

Then we demonstrated that sFRP-1 is a developmentally regulated gene during lung development. Immunohistochemistry results show that sFRP-1 is localized to the distal epithelial cells between day 13.5 and 15.5 and then expression is turned off. This expression colocalizes to the expression of wnt 10b. Thus, wnt 10b appears to be inhibited by sFRP-1 during lung development and possibly also in emphysema.

SFRP-1 is hypothesized to play a role in apoptosis. In this Example we demonstrate that apoptosis does occur in emphysema and most recently we have shown through transfection studies that increased expression of sFRP-1 leads to apoptosis in lung epithelial cells, endothelial cells and fibroblasts.

Methods

Histological Examination: Immunohistochemical staining was performed using mouse IgG to human proliferating cell nuclear antigen (PCNA) (clone PC 10, 1 mg/ml, Sigma, St. Louis, Mo.) and goat IgG to human sFRP1 (clone sc7425, 4 ug/ml, Santa Cruz Biotechnology, Santa Cruz, Calif.). For epitope retrieval of sFRP1, tissue sections were processed to the microwave treatment in 0.01 M sodium citrate buffer, pH 6.0 at 500 W. Biotinylated horse IgG to mouse IgG or FITC-labeled rabbit IgG to goat IgG were used as secondary antibodies. An avidin-biotin-peroxidase complex coupled with biotinylated hours IgG was visualized by 3,3'-diaminobenzidine tetrahydrochloride.

Apoptotic and Kproliferating Index: Percentage of TUNEL- or PCNA-reactive cells (apoptotic index and proliferation index, respectively) was mesured among over 3,000 lung parenchymal cells in randomly serected areas in each specimens at 40-fold magnification using light microscopy. The significance of difference in the apoptotic index or proliferation index among normal and four different clinical grade of emphysema was determined by one-way analysis of varience (ANOVA).

Protein Preparation and Analysis: For immunological detection of sFRP1, Western blot was performed using goat anti-sFRP1 antibody (1.5 mg/ml) and biotinylated rabbit IgG to goat IgG was used as a secondary antibody.

Transfection of Lung Cells with a sFrp1 Expression Vector: The mouse sFrp1 full length cDNA was generously provided by Drs. Jeremy Nathans and Amir Rattner, John Hopkins University, Baltimore, and subcloned into a pCMS-EGFP vector (Clontech, Palo Alto, Calif.). A gene of sFrp1w&s inserted into the multiple cloning site at EcoRI and Sail sites between the cytomegalovirus early promoter and SV40 polyadenilation signals, which direct proper processing of the 3' end of sFrp1 mRNA. The vector also has a Gfp (green fluorescent protein) gene located in downstream of the sFrp1-SV40 polyadenilation signals and ligated between the SV40 enhancer/promoter sequence and a polyadenylation signal from the bovine growth hormone gene. This vector construct allows transcriptions of sFrp1 and Gfp as separate proteins in transfected cells. Normal human primary cultured cells of small airway epithelial cells (SAEC 6043), lung microvascular endothelial cells (HMVEC L 6521-3), and lung fibroblasts (NHLF 5975) were obtained from BioWhittaker (Walkersville, Md.) and cultured in proper media containing 10% fetal bovine serum. Cells were plated 2 days before transfection in 4-well LabTek II chamber (Nalge Nunc International, Naperville, Ill.) at $2\times10^4$ cells/chamber and incubated at 37*C in 5% COj incubator. The sFrp1-Gjp expression vector or Gfp vector without sFrp gene (0.8 ujj) were transfected into cells using Lipofectaniine PLUS according to the manufacture's instruction (Gibco BRL). For Annexin-V-Biotin assay (Roche Diagnostics GmbH, Manheim, Germany), ceils were harvested at 72, 48, 24, 12 or 6 h after transfection and the reaction was detected by ExtraAvidin-Cy3 (Sigma). For caspase 3 activation assay, cells were fixed in 3% paraformaldehyde in PBS after 24 or 48 h of transfection and incubated with anti-human active caspase 3 antibody made by rabbit (x100, clone 9661. Cell Signaling Technology, Beverly, Mass.). Biotinylated goat IgG to rabbit IgG (Vector) and ExtraAvidin-Cy3 (Sigma) were used for detection of binding of a primary antibody.

Results

Correlation of Morphometric Measurements with Apoptotic Index and Proliferation Index.

Morphometric measurement showed progressive deterioration of lung architecture along with clinical grades of emphysema. The apoptotic index was increased as clinical grades of emphysema going to progressed but the index was decreased in the sever group. The statistical significance was observed between normal-mild, normal-moderate, and normal-sever. The mild grade also significantly higher of the prolifaration index than other grades. Through regression analysis the apoptotic index was shown to inversely correlate with the surface area demonstrating a close association of apoptosis and decrease of the lung surface area. Proliferation index did not have any correlation with apoptotic index and surface area. However, in normal lung, linear correlation was exhibited between proliferation index and apoptotic index. This initial correlation suggests that overcome of apoptotic activities to proliferation activities in emphysema lungs and vice versa.

Apoptosis-activation by sFrp1 expression. Transfection studies exhibited an apoptosis-inducing activity of sFrp1 without preference of cell-type examined. The activation of translocation of phosphatidylserine exposure to the outer cell membrane as detected by annexin V assay showed time- and dose-dependency of cell death to sFrp1 expression (data not shown). Fluorescent microscope indicated sFrp1 activity in autocine and paracrine fashion. Immunostaining analysis demonstrated the presence of acive caspase 3 in and surrounding cells transfected sFrp1, indicating apoptosis-activating activity of sFrp1. Further studies will be required to elucidate that an apoptosis-induction by sFrp1 activity is direct or indirect through inhibition of endogenous Wnt.

REFERENCES

1. From the centers for disease control and prevention. Mortality patterns—United States, 1991. JAMA, 1993, 270:2916-2917;
2. Feinleib M., et al. (1989) "Trends in COPD morbidity and mortality in the United States" Am Rev Respir Dis., 140:S9-18;
3. Snider G. L. (1989) "Chronic obstructive pulmonary disease: risk factors, pathophysiology and pathogenesis" Annu. Rev. Med., 40:411-429;
4. Snider G. L., et al. (1994) "Pitfalls in antiprotease therapy of emphysema" Am. J. Respir Crit. Care Med., 150:S131-S137;
5. Tetley T. D. (1993) "Proteinase imbalance: its role in the lung disease" Thorax, 48:560-565;
6. Shapiro S. D. (1995) "The pathogenesis of emphysema: the elastase:antielastase hypothesis 30 years later" Proc. Ass. Amer. Phys., 107:346-353;
7. D'Armiento J. et al. (1992) "Collagenase expression in the lungs of transgenic mice causes pulmonary emphysema" Cell, 71:955-961;
8. Putt F. (1972) Manual of Histopathological Staining Methods. New York: Wiley and Sons, 111-126;
9. Dunnill N. S. (1962) "Quantitative methods in the study of pulmonary pathology" Thorax, 17:320-328;
10. Thurlbeck W. M. (1967) "Internal surface area and other measurements in emphysema" Thorax, 22:486-496;
11. Tomkeiff S. E. (1945) "Linear intercepts, area and volumes" Nature, 155:105-111;
12. Imai K., et al. (1997) "Expression of membrane-type 1 matrix metalloproteinase and activation of progelatinase A in human oeteoarthritic cartilage" Am. J. Pathol., 151: 245-256;
13. Cardone M. H., et al. (1998) "Regulation of cell death protease caspase-9 by phosphorylation" Science, 282: 1318-1321;
14. Wyllie A. H. (1980) "Cell death: The significance of apoptosis" Int. Rev. Cytol., 68:251-306;
15. Wolf B. B. and Green D. R. (199) "Suicidal tendencies: Apoptotic cell death by caspase family proteinases" J. Biol. Chem., 274:20049-20052;
16. Frisch S. M. and Ruoslahti E. (1997) "Integrins and anoikis" Curr. Opin. Cell Biol., 9:701-706;
17. Petitclerc E., et al. (1998) "Integrin V3 promotes M21 melanoma growth in human skin by regulation tumor cell survival" Cancer Res., 59:2724-2730;
18. Luisetti M., et al. (1996) "MR889, a neutrophil elastase inhibitor, in patients with chronic obstructive pulmonary disease: a double-blind, randomized, placebo-controlled clinical trial" Eur. Resp. J., 9:1482-1486;
19. Granville D. J., et al. (1998) "Apoptosis: Molecular aspects of cell death and disease" Lab. Invest., 78:893-913;
20. Hoidal J. R. and Niewoehner D. E. (1983) "Pathogenesis of emphysema" Chest., 83:679-684;
21. Imai K. and D'Armiento J. (1999) "Activation of an embryonically expressed gene in pulmonary emphysema. Identification of the secreted frizzled-related protein" Am. Rev. Resp. Crit. Care Med., 159:A817;
22. Tetsu O. and McCormick F. (1999) b-catenin regulates expression of cyclin D1 in colon carcinoma cells. Nature 398:422-426;
23. Melkonyan H. S., et al. (1997) "SARPs: A family of secreted apoptosis-related proteins" Proc. Natl. Acad. Sci. USA 94:13636-13641;
24. Zhou Z., et al. (1998) "Up-regulation of human secreted frizzled homolog in apoptosis and its down-regulation in breast tumors" Int. J. Cancer, 78:95-99;
25. Ruddin C. M. and Thompson C. B. (1997) "Apoptosis and disease: Regulation and clinical relevance of programmed cell death" Annu. Rev. Med., 48:267-281;
26. Finch, P. W. et al. (1997) "Secreted frizzle related protein gene" Proc. Natl. Acad. Sci., 94:6770-6777.
27. Cherath, L. el al. in Laboratory Guide to RNA: Isolation, Analysis and Synthesis (ed. Kreig, P.) 251-271 (Wiley-Liss, Inc., New York, 1996)
28. Rattner, A. et al. A family of secreted proteins contains homology to the cysteine-rich ligand-binding domain of frizzled receptors. *Proc. Natl. Acad. Sci. USA* 94, 2859-2863(1997).
29. Hoang, B., Moos, M., Jr., Vukicevic, S. & Luyten, P. P. Primary structure and tissue distribution of FRZB, a novel protein related to Drosophilia frizzled, suggest a role in skeletal morphogenesis. *J. Biol. Chem.* 271, 26131-26137 (1996).
30. Melkonyan, H. S. et al. SARPs: A family of secreted apoptosis-related proteins. *Proc. Natl. Acad. Sci. USA* 94, 13636-13641 (1997).
31. Wnt Home Page created by Nusse, R. http://www.Stanford.edu/~rnusse/wntwindow.html.
32. Dale, T. C. Signal transduction by the Wnt family of ligands. *Biochem. J.* 329, 209-223 (1998).
33. Leyns, L. et al. Frzb-1 is a secreted antagonist of Wnt signaling expressed in the Spemann organizer. *Cell* 88, 747-756 (1997).
34. Fisk, D. E. & Kuhn, C. Emphysema-like changes in the lungs of the blotchy mouse. *Ann. Rev. Respir. Dis.* 113, 787-797 (1976).
35. Hautamaki, R. D., Kobayashi, D. K., Senior, R. M. & Shapiro, S. D. Requirement of macrophage elastase for, cigarette smoke-induced emphysema in mice. *Science* 277, 2002-2004(1997).
36. D'Armiento, J., Dalai, S. S. & Chada, K. Tissue temporal and inducible expression pattern of haptoglobin in mice. *Gene* 195, 19-27 (1997).
36. Hunter, T. Oncoprotein networks. *Cell* 88, 333-346 (1997).
37. Ashar, H. R. et al. Disruption of the architectural factor HMGI-C: DNA-binding AT hook motifs fused in lipomas to distinct transcriptional regulatory domains. *Cell* 82, 57-65(1995).

What is claimed is:

1. A method of identifying a compound effective to treat emphysema, comprising:

a) contacting lung cells from a subject having a emphysema with the compound and measuring the level of apoptosis of the lung cells in the presence of said compound, b) measuring the level of apoptosis of lung cells from the same subject in the absence of said compound, and c) comparing the level of apoptosis in step a) with the level of apoptosis in step b), wherein a higher level of apoptosis in step b) indicates that the compound is effective to treat emphysema.

2. The method of claim 1, wherein the level of apoptosis is determined by measuring DNA fragmentation or cleavage.

3. The method of claim 1, wherein the level of apoptosis is determined by measuring the expression of activated caspase 3.

4. The method of claim 1, wherein the level of apoptosis is determined by measuring the presence of poly(ADP ribose) polymerase.

5. The method of claim 1, wherein the level of apoptosis is determined by morphometric analysis.

6. The method of claim 1, wherein the level of apoptosis is determined by measuring Bcl-2 and/or Bad expression.

* * * * *